United States Patent
Brisson et al.

(10) Patent No.: US 7,244,875 B2
(45) Date of Patent: Jul. 17, 2007

(54) EXPRESSION VECTORS COMPRISING NUCLEIC ACIDS ENCODING SEBF PROTEINS AND USES THEREOF

(75) Inventors: Normand Brisson, Montreal (CA); Brian Boyle, Montreal (CA)

(73) Assignee: Valorisation-Recherche L.P., Quebec (CA)

( * ) Notice: Subject to any disclaimer, the term of this patent is extended or adjusted under 35 U.S.C. 154(b) by 287 days.

(21) Appl. No.: 10/483,448

(22) PCT Filed: Jun. 27, 2002

(86) PCT No.: PCT/CA02/00985

§ 371 (c)(1), (2), (4) Date: Jan. 7, 2004

(87) PCT Pub. No.: WO03/006659

PCT Pub. Date: Jan. 23, 2003

(65) Prior Publication Data

US 2005/0055741 A1    Mar. 10, 2005

Related U.S. Application Data

(60) Provisional application No. 60/303,780, filed on Jul. 10, 2001.

(51) Int. Cl.
*C12N 15/82* (2006.01)
*C12N 15/09* (2006.01)
*A01H 5/00* (2006.01)

(52) U.S. Cl. .............. 800/279; 800/278; 800/298; 435/69.1; 435/320.1; 435/468; 435/419

(58) Field of Classification Search ............. 800/278, 800/298; 435/468, 320.1
See application file for complete search history.

(56) References Cited

U.S. PATENT DOCUMENTS 6,100,456 A * 8/2000 Sticklen et al. .......... 800/317.2

OTHER PUBLICATIONS

Lazar et al. Molecular and Cellular Biology, Mar. 1988, vol. 8, No. 3, pp. 1247-1252.*
Broun et al. Science, Nov. 13, 1998, vol. 282, pp. 1315-1317.*
Van Der Hoeven, R., S., et al., "Generation of ESTS from Potato Leaves and Petioles", Database EMbl. Sequence Library Database Accession No. BE921879, Oct. 4, 2000.
Despres C. et al., "The Activation of the Potato PR-10A Gene Requires the Phosphorylation of the Nuclear Factor PBF-1", The Plant Cell, vol. 7, No. 5, May 1995, pp. 589-598.
Desveaux, Darrel et al., "PBF-2 is a Novel Single-Stranded DNA Binding Factor Implicated in PR-10A Gene Activation in Potato", The Plant Cell, vol. 12, No. 8, Aug. 2000, pp. 1477-1489.
Matton, Daniel, P., et al., "Identification of CIS-Acting Elements Involved in the Regulation of The Pathogenesis-Related Gene STH-2 in Potato", Plant Molecular Biology, vol. 22, No. 22, 1993, pp. 279-291.
Boyle, Brian et al., "Repression of the Defense Gene PR-10A by the Single-Stranded DNA Binding Protein SEBF", The Plant Cell, vol. 13, No. 11, Nov. 2001, pp. 2525-2537.

* cited by examiner

*Primary Examiner*—Medina A. Ibrahim
(74) *Attorney, Agent, or Firm*—Darby & Darby; Shelly M. Fujikawa

(57) ABSTRACT

The invention relates to vectors comprising nucleic acid sequences encoding transcriptional repressor silencing element binding factor referred as "SEBF", transformed vegetal host and plants comprising said vectors. The invention also relates to methods of altering resistance of a plant to pathogens with SEBF encoding nucleic acids.

**6 Claims, 7 Draw

Figure 3:
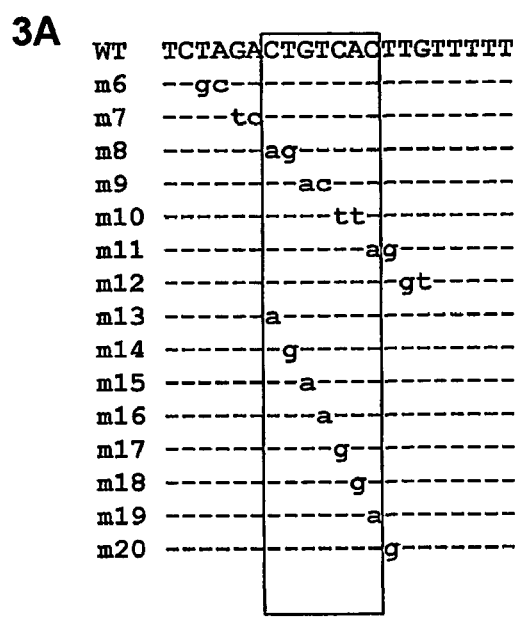
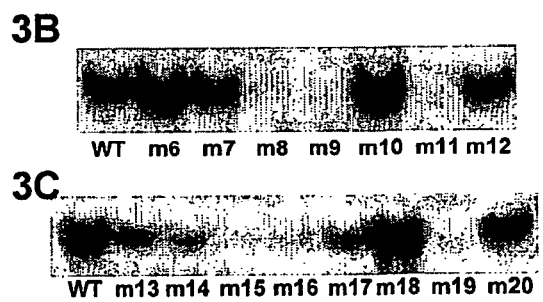
Figure 4:
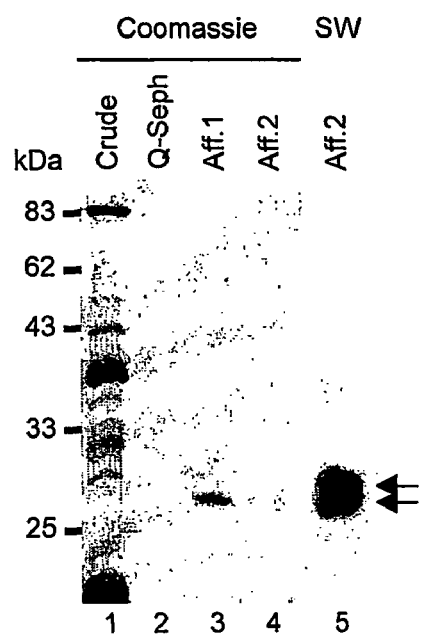

MASSSSSLHFLSLTPQTLPKPTSQTTSISFFSLPPSSLNL
SLSSSSTPRNFESSRFVRKVTLSDFDQIEEVEAGDDDEEE
GGLSDEGASYEERNANPDLKIFVGNLPFSVDSAALAELFE
RAGDVEMVEVIYDKLTGRSRGFGFVTMSSKEAVEAACQQF
NGYEIDGRALRVNSGPAPPKRENSFGDNSSYQGGRGGGSM
DSSNRVYVGNLAWSVDQQLETLFSEQGKVVDAKVVYDRD
SGRSRGFGFVTYSSAKEVNDAIESLDGVDLGGRAIRVSPA
EARPPRRQF

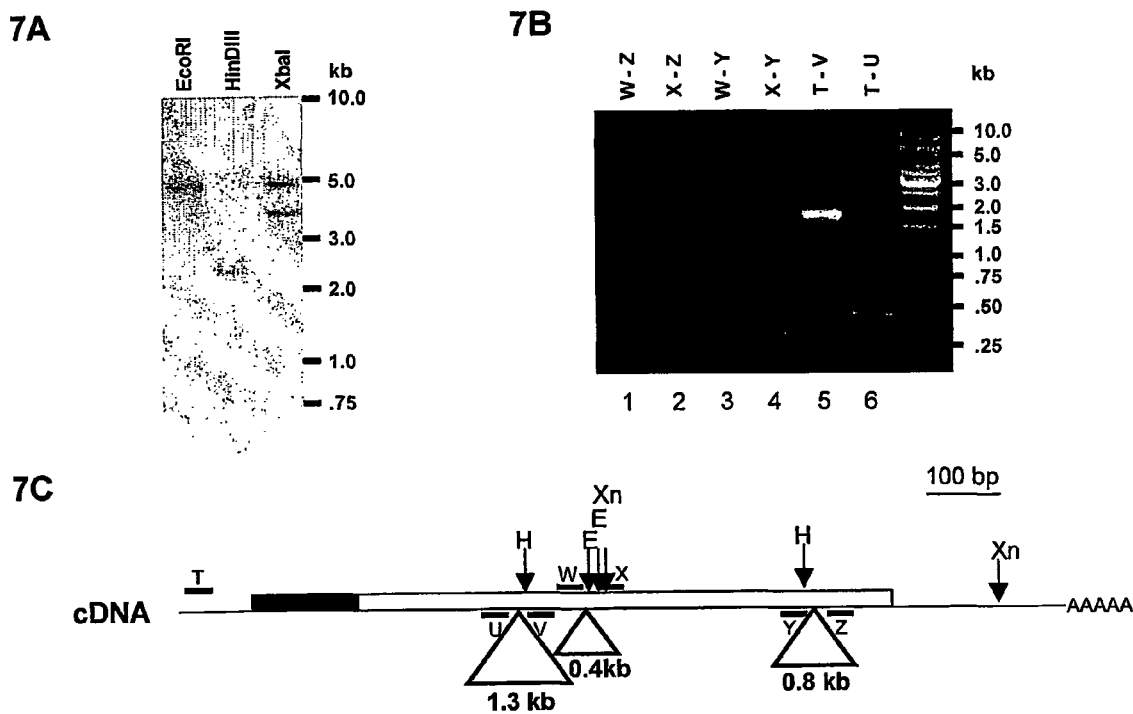

Figure 9    9A

```
PR-10a    TCTAGACTGTCACTTGTTTTTTTA
ChtC2     aacaTCTgcttTGTCAcctccTTg
CHN50     atTaagccaTGTCtCcatcaTcTTc
```

9B

PR-10a  ChtC2  CHN50

Figure 10:

```
1     GTTTTTCTTTTTCTGTCTTCACAATTCTTTTGCTTCAATAAAAACCTTATCTTCAACCCCTTCTCCAATGGCTTCTTCT
                                                                          M  A  S  S

81    CTTCTTCCCTCCATTTCCTTTCACTTACACCACAAACACTCCCAAAACCCACTTCCCAAACAACTTCAATTTCCTTCTTT
       S  L  H  F  L  S  L  T  P  Q  T  L  P  K  P  T  S  Q  T  T  S  I  S  F  F

161   TCACTTCCTCCTTCCTCTTTAAACCTTTCTTTATCATCTTCTTCAACCCCAAGAAACTTCGAATCTTCTCGTTTTGTTCG
       S  L  P  P  S  S  L  N  L  S  L  S  S  S  T  P  R  N  F  E  S  S  R  F  V  R

241   TAAAGTAACCCTTTCTGATTTTGACCAAATTGAGGAAGTTGAGGCTGGTGATGATGATGAGGAGGAGGGGGGTTTGAGTG
       K  V  T  L  S  D  F  D  Q  I  E  E  V  E  A  G  D  D  D  E  E  E  G  G  L  S  D

321   ATGAAGGTGCTTCATATGAAGAACGTAATGCCAATCCTGACCTTAAAATCTTTGTTGGTAATTTGCCTTTCAGTGTTGAC
       E  G  A  S  Y  E  E  R  N  A  N  P  D  L  K  I  F  V  G  N  L  P  F  S  V  D

401   AGTGCGGCTCTTGCTGAGCTTTTTGAGCGTGCTGGAGATGTTGAAATGGTTGAGGTTATCTATGACAAGCTTACAGGAAG
       S  A  A  L  A  E  L  F  E  R  A  G  D  V  E  M  V  E  V  I  Y  D  K  L  T  G  R

481   AAGCAGAGGTTTTGGCTTTGTGACAATGTCCTCCAAAGAGGCAGTTGAAGCCGCCTGTCAACAATTTAATGGCTATGAAA
       S  R  G  F  G  F  V  T  M  S  S  K  E  A  V  E  A  A  C  Q  Q  F  N  G  Y  E  I

561   TTGACGGGAGGGCACTGAGGGTGAATTCTGGGCCAGCACCACCCAAAAGGGAGAATTCTTTCGGGGACAATTCTTCTTAC
       D  G  R  A  L  R  V  N  S  G  P  A  P  P  K  R  E  N  S  F  G  D  N  S  S  Y

641   CAGGGAGGTAGGGGTGGAGGGAGTATGGACAGTTCCAACAGAGTCTACGTAGGAAACCTTGCATGGAGTGTTGACCAACA
       Q  G  G  R  G  G  G  S  M  D  S  S  N  R  V  Y  V  G  N  L  A  W  S  V  D  Q  Q

721   GCAACTTGAGACCTTGTTCAGTGAGCAAGGAAAGGTCGTGGATGCCAAAGTAGTCTATGATAGAGATAGCGGTAGATCAA
       Q  L  E  T  L  F  S  E  Q  G  K  V  V  D  A  K  V  V  Y  D  R  D  S  G  R  S  R

801   GGGGCTTTGGATTTGTAACATACAGTTCCGCTAAGGAGGTCAACGATGCAATTGAAAGCTTGGATGGTGTTGACCTAGGT
       G  F  G  F  V  T  Y  S  S  A  K  E  V  N  D  A  I  E  S  L  D  G  V  D  L  G

881   GGCAGGGCCATCCGTGTAAGTCCTGCTGAAGCTCGTCCACCCAGACGTCAATTCTGAAGATTGTAGCCAACATCTTTTTG
       G  R  A  I  R  V  S  P  A  E  A  R  P  P  R  R  Q  F

961   ACCGAGAAAAGGCTTGAGGGTCCAGGAGGTGACGATAGTTGCAGAAATGAATGAGTTATGAACTTTGCAACAGCTATCTT

1041  AAACTTGCGCGGACAAACTACTCTCTACTTCTGGACTAACTAGAGCTCTCAAGTAAATTAGTTTTCGTAATGTATGTTCT

1121  GAAATTGCCTCAGGAAGAAATTCTGATCTTGTAATATGATTCTATCCATCACTTGTTGACAGACAAGACAATGAAAAAGT

1201  TTGATACTCTTCGAAAAAG
```

11A

SEBF        BTGTCNC
AuxRE       TGTCNC

11B

SE (*PR-10a*)   CTGTCAC
D4 (*GH3*)      TTGTCTC

11C

Figure 12:
FIGURE 12A
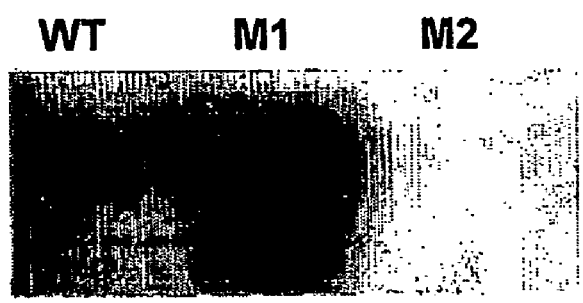
FIGURE 12B
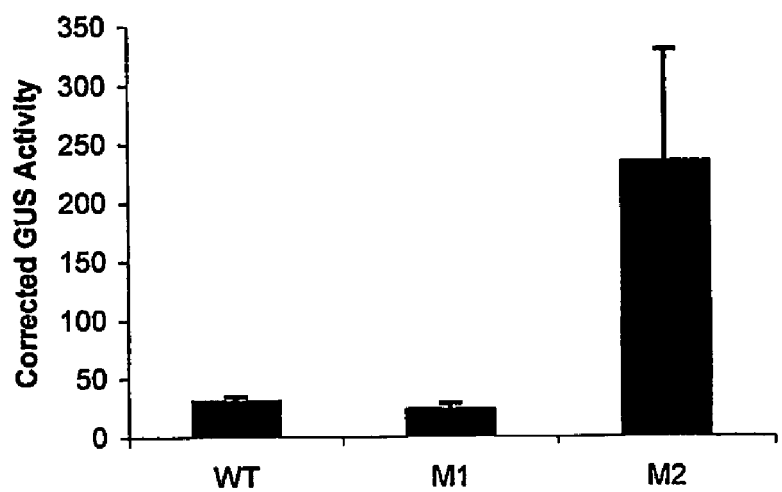
FIGURE 12C
| | |
|---|---|
| WT | TAAGCCATGTCTCCATCATCT |
| M1 | TAAGCC<u>c</u>TGTCTCCATCATCT |
| M2 | TAAGCCAT<u>a</u>TCTCCATCATCT |

EXPRESSION VECTORS COMPRISING NUCLEIC ACIDS ENCODING SEBF PROTEINS AND USES THEREOF

RELATED APPLICATION

This application claims priority of U.S. Provisional Application 60/303,780 filed Jul. 10, 2001, the disclosure of which is incorporated by reference herein in its entirety.

BACKGROUND OF THE INVENTION

A) Field of the Invention

The present invention relates to a plant gene regulatory element and its uses, and more particularly to a silencing element for modulating plant responses to pathogens, auxin and ethylene. The invention also relates to transcriptional repressors which specifically binds onto the silencing element of the invention, including a protein referred herein after as "SEBF".

B) Brief Description of the Prior Art

A variety of defense specific events are induced in plants in response to pathogen infection. Although key components of the signaling cascades are being discovered, few transcription factors that integrate these signals at the transcriptional level have been identified up to date.

PR genes are plant genes that are induced by pathogen invasion. These genes are subdivided into 11 classes. Since PR genes are well characterized, they provide excellent models to study transcriptional regulation of defense genes.

The PR-10 gene family is one of the classes of PR genes. Expression studies have identified cis-acting elements involved in PR-10a gene regulation, a member of the PR-10 gene family. An elicitor response element (ERE) located between nucleotides −135 and −105 is essential and sufficient for elicitor induced expression of PR-10a. PBF-2, a single-stranded DNA binding factor, appears to play a role in activation of PR-10a from the ERE. It has been shown that the presence of the ERE is sufficient for PR-10a activation, removal of the silencing element (SE), located between −52 and −27, leads to further activation, suggesting that SE participates, with the ERE, in the regulation of PR-10a (Matton et al, 1993; Després et al., 1995). However, the exact nucleic acid sequence required for full SE activity has never been given. Furthermore, the identity of the transcriptional repressor specifically binding to the silencing element (SE) of PR-10a is also unknown.

Accordingly, there is a need for an isolated or purified nucleic acid comprising a sequence coding for full of SE activity and to the use thereof for modulating activity of genes, and more particularly genes involved in plant responses to pathogen such as PR-10a gene. There is also a need for methods and genetically modified plants wherein the nucleic acid of the invention has been introduced or wherein the sequence coding for full SE activity has been mutated, deleted, or silenced, thereby modulating the plant defense mechanisms and resistance to pathogens.

There is also a long felt need for a transcriptional repressor that is capable of modulating plant defense mechanisms and resistance to pathogens and more particularly for a transcriptional repressor capable to specifically bind the isolated or purified nucleic acid of the invention. There is also a need for methods and genetically modified plants wherein levels of the transcriptional repressor of the invention have been modulated.

There is a further need for effective methods and compositions to modulate plant resistance or tolerance to pathogens, and/or to modulate plant response to auxin and/or to ethylene.

The present invention fulfills these needs and also other needs which will be apparent to those skilled in the art upon reading the following specification.

SUMMARY OF THE INVENTION

According to a first aspect, the present invention relates to an isolated or purified nucleic acid molecule comprising a sequence selected from the group consisting of:
a) sequence set forth in SEQ ID NO: 21;
b) a nucleotide sequence having at least 96% nucleotide sequence identity with SEQ ID NO: 21; and
c) a nucleotide sequence having at least 75% nucleotide sequence identity with a nucleic acid encoding an amino acid sequence of SEQ ID NO:22.

The invention also concerns transformed or transfected cells as well as cloning or expression vector that contains such a nucleic acid. Preferably, the cell and the vector express or are capable of directing expression of the peptide encoded by the nucleic acid.

In a related aspect, the invention concerns an isolated or purified protein comprising an amino acid sequence selected from the group consisting of:
a) sequences encoded by a nucleic acid as defined previously;
b) sequences having at least 85% identity to SEQ ID NO: 22;
c) sequences having at least 87% similarity to SEQ ID NO: 22;
d) sequence set forth in SEQ ID NO: 22;
e) sequences having at least 85% identity to amino acid sequences encoded by nucleotides 68 to 937 of SEQ ID NO: 21; and
f) sequences having at least 87% sequence similarity to amino acid sequences encoded by nucleotides 68 to 937 of SEQ ID NO: 21.

The inventions also concerns compositions comprising any of the nucleic acids or protein defined previously.

In another aspect, the invention relates to plant proteinic nuclear factors that are capable, among other things, of mediating repression of a silencing element involves in plant defense mechanisms. Preferably, the proteinic nuclear factor is a plant transcriptional repressor which specifically binds onto the sequence BTGTCNC or YTGTCNC. Most preferred transcriptional repressor consists of a protein referred herein after as "SEBF" for Silencing Element Binding Factor. In one embodiment there is described a composition comprising an isolated or purified SEBF protein or a functional homologue thereof. Preferably, the SEBF protein or homologue comprises an amino acid sequence selected from the group consisting of:
a) sequences encoded by a nucleic acid having a sequence at least 85% identical to nucleotides 68 to 937 of SEQ ID NO: 21;
b) sequences having at least 85% identity to SEQ ID NO:22;
c) sequences having at least 87% similarity to SEQ ID NO:22; and
d) sequence provided in SEQ ID NO:2.

More preferably, the SEBF protein is purified from potato, and wherein it has a purification factor of about 90 to about 20 700 fold.

According to another aspect, the present invention relates to an isolated or purified nucleic acid comprising a binding sequence onto which proteinic nuclear factors, such as the transcriptional repressor of the silencing element (SE) of PR-10a, specifically binds. Preferably, the binding sequence comprises sequence BTGTCNC (SEQ ID NO:23), more preferably sequence YTGTCNC (SEQ ID NO:24). The invention also concerns an isolated or purified gene regulatory element comprising a nucleic acid sequence that is essential for the full activity in plant of the silencing element (SE) of PR-10a. Preferably, the gene regulatory element consists of a silencing element and it comprises sequence GACTGTCAC (SEQ ID NO:26) or sequence BTGTCNC (SEQ ID NO:23), and more preferably sequence YTGTCNC (SEQ ID NO:24). The invention also concerns a DNA construct comprising the gene regulatory element and genetically modified plant entities comprising the gene regulatory element or the DNA construct.

According to a related aspect, the present invention concerns a method for altering gene expression in a plant. The method comprises the step of altering in the plant binding of a nuclear DNA-binding protein to sequence BTGTCNC. A non-limitative list of preferred endogenous DNA-binding proteins includes those having at least 48% identity or similarity to SEBF. More preferably, the DNA-binding protein consists of SEBF or of a functional homologue thereof having at least 90% identity or similarity to SEBF.

In a preferred embodiment, there is described a method for increasing the expression of a gene of interest, this gene having a promoter region comprising sequence BTGTCNC. The method comprises the step of mutating the promoter region of the gene for mutating or deleting the sequence BTGTCNC. The gene maybe PR gene.

In another preferred embodiment, there is described a method for reducing the expression of a gene of interest, this gene having a promoter region devoid of sequence BTGTCNC. The method comprises the step of introducing in an operable linked manner the sequence BTGTCNC into the promoter region.

In a more specific embodiment, there is described a vegetal host (e.g. algae, plant) genetically modified for exhibiting an altered expression or biological activity of a proteinic nuclear factor having a specific binding activity to sequence BTGTCNC (SEQ ID NO:23), preferably YTGTCNC (SEQ ID NO:24), the altered level being compared to a corresponding genetically unmodified vegetal host in which the endogenous level has not been altered. Preferred proteinic nuclear factors are those having at least 48% identity or similarity to SEBF. More preferably, the proteinic nuclear factors consists of SEBF or of a functional homologue thereof having at least 90% identity or similarity to SEBF.

In an even more specific embodiment, the expression or biological activity of SEBF or homologue has been increased in the vegetal host such that it exhibits a phenotype selected from the group consisting of:
reduced resistance or tolerance to a pathogen;
reduced growth, rooting and/or fruit production;
increased resistance to an auxinic herbicide;
reduced ethylene production;
delay in ripening of its fruit(s) and/or protection of its fruit(s) against over-ripening.

In an other specific embodiment, the expression or biological activity of SEBF or homologue has been reduced in the vegetal host such that it exhibits a phenotype selected from the group consisting of
increased resistance or tolerance to a pathogen;
increased growth, rooting and/or fruit production;
increased sensitivity to an auxinic herbicide;
increased ethylene production; and
early fruit maturation.

The invention also encompasses methods for obtaining the vegetal host having the phenotype(s) described previously. Typically these methods comprises the step of modulating (typically reducing or increasing) in the plant expression or biological activity of SEBF or of a SEBF functional homologue.

Another related aspect of the invention concerns a genetically modified vegetal host comprising a genome, wherein transcriptional activity of a gene associated with presence or absence of sequence BTGTCNC (SEQ ID NO:23), preferably YTGTCNC (SEQ ID NO:24), in a promoter region this gene has been altered. Of course, the altered biological activity is compared to a corresponding genetically unmodified vegetal host in which the endogenous biological activity has not been altered.

In one embodiment, the promoter region of the gene comprises the sequence BTGTCNC, and the promoter region has been genetically modified (e.g. mutation, deletion) for inactivating a repressive transcriptional activity associated with the presence of the sequence BTGTCNC.

In another embodiment, the promoter region is devoid of sequence BTGTCNC (SEQ ID NO:23), and this region has been genetically modified for inserting therein in an operable linked manner the sequence BTGTCNC.

In another aspect, the present invention relates to methods for obtaining a particular phenotype in plants, and more particularly plants which are used in agriculture and plants with a horticultural value. In one embodiment, there is described methods for:
the modulation of a plant resistance or tolerance to pathogens;
the modulation of induction of genes of a plant controlled by auxins;
the modulation of a plant auxins-controlled genes induction;
the augmentation of growth, rooting and/or fruit production in a plant;
the modulation of a plant auxin-inducted ACC synthase gene;
the modulation of a plant ethylene production; and
the modulation of a plant plastid mRNAs stability, expression or activity.

All these methods comprises the step of modulating in the plant expression or biological activity of an endogenous SEBF protein or of a SEBF functional homologue.

In one preferred embodiment, there is described a method for obtaining a genetically modified plant exhibiting a phenotype selected from the group consisting of:
increased resistance or tolerance to a pathogen;
increased growth, rooting and/or fruit production;
increased sensitivity to an auxinic herbicide;
increased ethylene production;
early fruit maturation;
altered plastid mRNAs stability, expression or activity;
a promoter region of a gene involved in the phenotype comprising sequence BTGTCNC (SEQ ID NO:23), the phenotype of the plant being compared to a corresponding genetically unmodified plant;
the method comprising the step of genetically modifying the genome of this plant for inactivating an endogenous biological activity associated with the presence of the sequence BTGTCNC.

In one preferred embodiment, there is described a method for obtaining a genetically modified plant exhibiting a phenotype selected from the group consisting of:

reduced resistance or tolerance to a pathogen;
reduced growth, rooting and/or fruit production;
increased resistance to an auxinic herbicide;
reduced ethylene production;
delay in ripening of its fruit(s) and/or protection of its fruit(s) against over-ripening; and
altered plastid mRNAs stability, expression or activity;
a promoter region of a gene involved in the phenotype being devoid of sequence BTGTCNC (SEQ ID NO:23), the phenotype of the plant being compared to a corresponding genetically unmodified plant;
the method comprising the step of genetically modifying the genome of said plant for inserting therein in an operably linked manner the sequence BTGTCNC.

In further embodiments of the invention, there is described plants, and methods for obtaining the same, the plants exhibiting an increased (or decreased) resistance or tolerance to pathogens; a faster (or lower) induction of its defense response; an increased (or decreased) sensitivity for endogenous auxins; and/or a delayed ripening or an advanced fruit maturation.

In one specific embodiment, there is provided a method for modulating a plant resistance or tolerance to a pathogen, comprising modulating in the plant expression or biological activity of an endogenous SEBF protein. More particularly, the is described a method for increasing a plant resistance or tolerance to a pathogen, comprising reducing in the plant expression or biological activity of an endogenous SEBF protein. Expression or biological activity of the endogenous SEBF protein may be reduced increased for instance by expressing in the plant SEBF antisense molecules; by expressing proteins inducing a co-suppression of SEBF level or activity; by a knock out or a chemical mutagenesis of a gene encoding the SEBF protein; of by expressing a ribozyme cleaving a SEBF mRNA. The is also described a method for reducing a plant resistance or tolerance to a pathogen, comprising increasing in the plant expression or biological activity of a SEBF protein. The expression or biological activity of the endogenous SEBF protein may increased for instance by introducing in the plant a expressible SEBF coding sequence. The SEBF coding sequence may be under control of an inducible or constitutive promoter. The invention also encompasses plants genetically modified for having an increased (or reduced) resistance or tolerance to a pathogen when compared to a corresponding plant not genetically modified, wherein expression or biological activity of an endogenous SEBF protein is reduced (or increased) in the genetically modified plant as compared to a corresponding genetically unmodified plant.

In a another specific embodiment, there is provided a method for modulating a plant resistance or tolerance to a pathogen, the plant having sequence BTGTCNC (SEQ ID NO:23) in a promoter region of a gene, the method comprising altering in this plant the binding of an endogenous nuclear DNA-binding protein to the sequence BTGTCNC. More particularly, the is described a method for increasing a plant resistance or tolerance to a pathogen, the plant having sequence BTGTCNC (SEQ ID NO:23) in a promoter region of a gene, the method comprising reducing or preventing in the plant binding of an endogenous nuclear DNA-binding protein to the sequence BTGTCNC. The is also described a method for reducing a plant resistance or tolerance to a pathogen, comprising permitting or increasing in said plant binding of an endogenous nuclear DNA-binding protein to a promoter region of a gene including sequence BTGTCNC (SEQ ID NO:23). The invention also encompasses plants genetically modified by these methods for having an increased (or reduced) resistance or tolerance to a pathogen.

In a further specific embodiment, there is provided a method for modulating induction of genes controlled by auxins in plants, the method comprising modulating in the plant expression or biological activity of an endogenous SEBF protein or of a SEBF functional homologue. More particularly, the is described a method for increasing growth, rooting and/or fruit production in a plant, the method comprising reducing in the plant expression or biological activity of an endogenous SEBF protein or of a SEBF functional homologue. There is also described a method for increasing a plant resistance to an auxinic herbicide, comprising reducing in the plant expression or biological activity of an endogenous SEBF protein or of a SEBF functional homologue. The invention also encompasses plants genetically modified by these methods.

In still a further specific embodiment, there is provided a method for modulating a plant ethylene production, comprising modulating in the plant expression or biological activity of an endogenous SEBF protein or of a SEBF functional homologue. More particularly, the is described a method for increasing production of ethylene by a plant, comprising reducing in the plant expression or biological activity of an endogenous SEBF protein or of a SEBF functional homologue. There is also described a method for reducing production of ethylene by a plant, comprising increasing in the plant expression or biological activity of an endogenous SEBF protein or of a SEBF functional homologue. The invention also encompasses plants genetically modified by these methods for having an increased (or reduced) production of ethylene.

As used hereinbefore, the vegetal host preferably consists of a plant (monocotyledon or dicotyledon), more preferably a vegetable, a leguminous plant, a tree, a fruit tree, grass, a cereal, and even more preferably it consists of a potato, a tomato, tobacco, cotton, rice, wheat, corn, barley, oat, canola, soybean, pea, sugar cane, sugar beet, strawberry, and banana.

Other objects and advantages of the present invention will be apparent upon reading the following non-restrictive description of several preferred embodiments, made with reference to the accompanying drawings.

BRIEF DESCRIPTION OF THE DRAWINGS

FIG. 2A: Schematic representation of the reporter constructs and mutant oligonucleotides used in this study. Reporter constructs contain the PR-10a promoter region from −135 to +136 fused to the bacterial gene uidA encoding β-glucuronidase (GUS). The position of the elicitor response element (ERE), the silencing element (SE) and the TATA box are shown (TATA). The transcriptional start site is indicated by an arrow. The common sequence between the wild-type (WT; SEQ ID NO:45) and mutant oligonucleotides m1 to m5 (SEQ ID NOs:1 to 5) is indicated by dashed lines, and mutated nucleotides are represented by lowercase letters. FIG. 2B: EMSA studies using 10 µg of crude potato tuber nuclear preparation and 20,000 CPM of the $^{32}$P labeled single-stranded CS oligonucleotides presented in FIG. 2A. FIG. 2C: EMSA studies using 10 ng of purified recombinant SEBF and 20,000 CPM of the $^{32}$P labeled single-stranded CS oligonucleotides presented in FIG. 2A. FIG. 2D: The sequence from −52 to −27 of the PR-10a promoter fused to the uidA gene was replaced by the sequences presented in FIG. 2A. The resulting plasmids were electroporated in potato leaf protoplasts and the GUS activity was measured. The histogram represents fold activity to wild type (WT=1). Transfection efficiencies were corrected by co-electroporating a luciferase reporter gene. Results represent the mean from a minimum of 6 individual electroporations. Error bars indicate the standard deviation of the mean.

FIGS. 3A, 3B and 3C show results leading to the determination of the consensus SEBF binding site. FIG. 3A: Oligonucleotides used for fine mapping of the SEBF binding site are listed. The common sequence between wild-type (SEQ ID NO:46) and mutant oligonucleotides m6 to m20 (SEQ ID NOS:6 to 20) is indicated by dashed lines. Mutated nucleotides are represented by lowercase letters. FIG. 3B: EMSA showing the binding of SEBF to oligonucleotides containing two mutated nucleotides. FIG. 3C: As in FIG. 3B except oligonucleotides containing single mutation. Studies were performed using 10 µg of crude nuclear preparation and 20,000 CPM of $^{32}$P labeled single-stranded oligonucleotides presented in FIG. 3A.

FIG. 4 is a picture of a gel showing the purification of SEBF. Coomassie staining of proteins from each step of the purification of SEBF (lanes 1 through 4). The crude nuclear extract (Crude; lane 1) was loaded on a Q-Sepharose™ column. SEBF was eluted at 400 mM NaCl (Q-seph; lane 2) before two rounds of affinity purification (Aff.1, Aff.2; lane 3, lane 4). Lane 5 shows a southwestern (SW) experiment done with affinity 2 purified SEBF and the wild type coding strand as a radiolabeled probe. Arrows indicate the two purified bands. Molecular weight markers are indicated on the left.

FIGS. 7A, 7B and 7G show the genomic organization of SEBF. FIG. 7A: Southern blot of SEBF. Five µg of digested genomic DNA was loaded per lane and probed with a random-labeled Xmnl fragment from the SEBF cDNA shown in FIG. 7C. Molecular markers are indicated on the right. FIG. 7B: PCR analysis of the genomic DNA. The position of the oligonucleotides (1 to Z; lane 1 to 6) on the cDNA is presented in FIG. 7C. The difference in size between the amplification products of lanes 5 and 6, lanes 3 and 4, and lanes 2 and 4, define the size of introns 1, 2 and 3 respectively. Molecular weight markers are indicated on the right. FIG. 7C: Deduced genomic organization of SEBF. The cDNA is represented as a line and the coding region as a box. The amino terminal transit sequence is presented in black. Introns are indicated as triangles emerging from the cDNA. The oligonucleotides used in the PCR reactions are designated by letters (T, U, V, W, X, Y, Z; corresponding to SEQ ID NOS: 38 to 44). The position and size of the introns are deduced from the PCR analysis FIG. 7B. Restriction sites are indicated by arrows: HinDIII (H), EcoRI (E), Xmnl (Xn).

FIG. 8 shows that SEBF overexpression represses PR-10a expression. The coding sequence of precursor SEBF (containing the putative transit peptide) and the coding sequence of a control protein were each inserted into plasmid pBI223D (Effector Plasmids). These plasmids were co-electroporated in potato leaf protoplasts with the reporter plasmids described in FIG. 2D (Reporter Plasmids). The histogram represents the effect of SEBF overexpression on reporter activity compared to the overexpression of the control protein (control=100). Fold activity to wild type SE (WT=1) is presented for easier reference to FIG. 2D. Transfection efficiencies were corrected by co-electroporating a luciferase reporter gene. Results represent the mean from a minimum of 3 individual electroporations. Error bars indicate the standard deviation of the mean.

FIGS. 9A and 9b show that SEBF binds the promoter of other defense genes. FIG. 9A: Oligonucleotides used in this experiment are listed. Nucleotides diverging from PR-10a (SEQ ID NO: 25 and 47; corresponding to nucleotides 1426 to 1450 of Genbank™ acc. No. M29041) are represented by lowercase letters. The SEBF binding site is underlined. ChtC2 is a chitinase gene from potato (SEQ ID NO:48, corresponding to nucleotides 1264 to 1288 of Genbank™ acc. No. AF153195) and CHN50 is a chitinase gene from tobacco (SEQ ID NO:49, corresponding to nucleotides 1215 to 1239 of Genbank™acc. No. X51599). FIG. 9B: EMSA studies using 0.5 µg of 400 mM Q-Sepharose fraction and 20,000 CPM of the $^{32}$P labeled single-stranded oligonucleotides presented in FIG. 9A.

FIG. 10 shows the DNA (SEQ ID NO:21) and protein (SEQ ID NO:22) sequence of SEBF (GenBank™ acc. No. AF38431). The translated protein (see FIG. 5; SEQ ID NO:22) is indicated below the DNA sequence. Each amino acid is indicated below the first nucleotide of the codon.

FIG. 11A: Comparison of the SEBF binding site (SEQ ID NO:23) with the AuxRE (SEQ ID NO:55). FIG. 11B: Oligonucleotides used in this study (SEQ ID NOS:50 and 51). FIG. 11C: EMSA was performed with 0.5 µg of a 400 mM Q-sepharose™ fraction and 20,000 CPM of $^{32}$P labeled oligonucleotides presented in FIG. 11B.

FIGS. 12A, 12B and 12C show the functionality of the SE sequence in the promoter of the defense gene CHN50. FIG. 12A: EMSA was performed with 0.5 µg of a 400 mM Q-sepharose™ fraction and 20,000 CPM of $^{32}$P labeled oligonucleotides presented in FIG. 12C. FIG. 12B: The CHN50 promoter, or mutated versions shown in FIG. 12C, were fused to the uidA gene. The resulting plasmids were electroporated in tobacco leaf protoplasts and the GUS activity was measured. Transformation efficiencies were corrected by co-electroporating a luciferase reporter gene. Results represent a minimum of three individual electroporations. Error bars indicate the standard deviation of the mean. FIG. 12C: oligonucleotides used in this study (WT=SEQ ID NO:52; M1=SEQ ID NO:53; M2=SEQ ID NO:54). Mutations are represented by lowercase letters and are underlined. The SEBF binding site is indicated in boldface characters.

DETAILED DESCRIPTION OF THE INVENTION

A) Definitions

Figure 1:
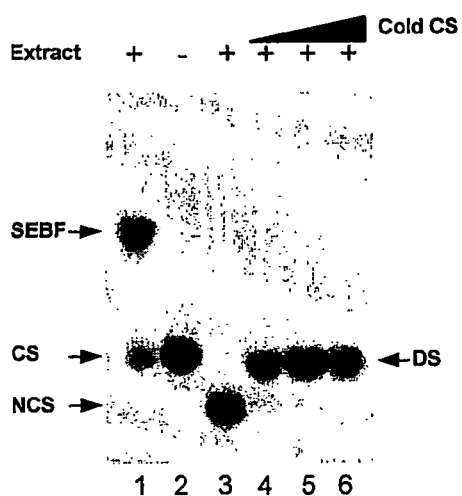
FIG. 1 is a picture of a gel showing binding of SEBF to a single-stranded silencing element. EMSA was performed with 10 µg of crude nuclear preparation and 20,000 CPM of $^{32}$P labeled SE coding strand (lane 1; CS) or non-coding strand (lane 3; NCS). The double-stranded probe (DS) was made by annealing radiolabeled non-coding and non-labeled (cold) coding strand. The ratio CS:NCS is 0.75:1, 1.5:1 and 3:1 for lanes 4 through 6, respectively. No extract was added in lane 2. Arrows indicate the position of the CS, NCS and DS probes and of the SEBF shift in the gel.

In order to provide an even clearer and more consistent understanding of the specification and the claims, including the scope given herein to such terms, the following definitions are provided:

Antisense: Refers to nucleic acids molecules capable of regulating the expression of a corresponding gene in a plant. An antisense molecule as used herein may also encompass a gene construct comprising a structural genomic gene, a cDNA gene or part thereof in reverse orientation relative to its or another promoter. Typically antisense nucleic acid sequences are not template for protein synthesis but yet interact with complementary sequences in other molecules (such as a gene or RNA) thereby causing the function of those molecules to be affected.

Chemical derivative: As used herein, a protein/polypeptide is said to be a "chemical derivative" of another protein/polypeptide when it contains additional chemical moieties not normally part of the protein/peptide, said moieties being added by using techniques well known in the art. Such moieties may improve the protein/polypeptide solubility, absorption, bioavailability, biological half life, and the like. Any undesirable toxicity and side-effects of the protein/peptide may be attenuated and even eliminated by using such moieties. For example, proteins/polypeptides can be covalently coupled to biocompatible polymers (polyvinyl-alcohol, polyethylene-glycol, etc) in order to improve stability or to decrease/increase their antigenicity.

Defence gene: A gene that is induced and/or involved in a plant response to a pathogen challenge.

Fragment: refers to a section of a molecule, such as protein/polypeptide or nucleic acid, and is meant to refer to any portion of the amino acid or nucleotide sequence.

Functional homologue: As is generally understood and used herein, refers to non-native a polypeptide or a nucleic acid molecule that possesses a functional biological activity that is substantially similar to the biological activity of a native polypeptide or a nucleic acid molecule. Preferred functional homologue are polypeptides or nucleic acid molecules having a sequence "substantially identical" (see hereinafter) to the native polypeptide or a nucleic acid molecule. The functional homologue may exist naturally or may be obtained following a single or multiple amino acid substitutions, deletions and/or additions relative to the naturally occurring enzyme(s) using methods and principles well known in the art. A functional homologue of a protein may or may not contain post-translational modifications such as covalently linked carbohydrate, if such modification is not necessary for the performance of a specific function. It should be noted, however, that nucleotide or amino acid sequences may have similarities below the above given percentages and still encode a proteinic molecule having a desired activity, and such proteinic molecules may still be considered within the scope of the present Invention where they have regions of sequence conservation. The term "functional homologue" is intended to the "fragments", "segments", "variants", "analogs" or "chemical derivatives" of a polypeptide or a nucleic acid molecule.

Fusion protein: A protein formed by the expression of a hybrid gene made by combining two gene sequences. Typically, this is accomplished by cloning a cDNA into an expression vector in frame with an existing gene.

Genetic modification: When used with the term "vegetal host" or "plant" it refers to the introduction of an exogenous nucleic acid into one or more vegetal host (plant) cells to create a genetically modified vegetal host or plant. Methods for genetically modifying vegetal host such as plants are well known in the art. In some cases, in may be preferable that the genetic modification is permanent such that the genetically modified plant may regenerate into whole, sexually competent, viable genetically modified plants. A plant genetically modified in a permanent manner would preferably be capable of self-pollination or cross-pollination with other plants of the same species, so that the exogenous nucleic acid, carried in the germ line, may be inserted into or bred into agriculturally useful plant varieties.

Endogenous or Endogenous level(s): Refers to a given substance or to the concentration of a given substance which is normally found in a plant (intrinsic) at a given time and stage of growth. The term also includes functional homologues of a given substance or protein which may results from a mutation. Reference herein is made to the altering of the endogenous level of a compound or of an enzyme activity relating to an elevation or reduction in the compound's level or enzyme activity of up to 30% or more preferably of 30, 35, 40, 45 or 50%, or even more preferably 55, 60, 65, 70 or 75% or still more preferably 80, 85, 90, 95% or greater above or below the normal endogenous or existing levels. The levels of a compound or the levels of activity of an enzyme can be assayed using known method and techniques.

Expression: refers to the process by which gene encoded information is converted into the structures present and operating in the cell. In the case of cDNAs, cDNA fragments and genomic DNA fragments, the transcribed nucleic acid is subsequently translated into a peptide or a protein in order to carry out its function if any. The term "overexpression" refers to an upward deviation respectively in assayed levels of expression as compared to a baseline expression level which is the level of expression that is found under normal conditions and normal level of functioning. Similarly, the term "underpression" refers to an downward deviation. By "positioned for expression" is meant that the DNA molecule is positioned adjacent to a DNA sequence which directs transcription and translation of the sequence (i.e., facilitates the production of, e.g., a NAIP polypeptide, a recombinant protein or a RNA molecule).

Isolated or Purified or Substantially pure: Means altered "by the hand of man" from its natural state, i.e., if it occurs in nature, it has been changed or removed from its original environment, or both. For example, a polynucleotide or a protein/peptide naturally present in a living organism is not "isolated", the same polynucleotide separated from the coexisting materials of its natural state, obtained by cloning, amplification and/or chemical synthesis is "isolated" as the term is employed herein. Moreover, a polynucleotide or a protein/peptide that is introduced into an organism by transformation, genetic manipulation or by any other recombinant method is "isolated" even f it is still present in said organism.

Modulation: Refers to the process by which a given variable is regulated to a certain proportion.

Nucleic acid: Any DNA, RNA sequence or molecule having one nucleotide or more, including nucleotide sequences encoding a complete gene. The term is intended to encompass all nucleic acids whether occurring naturally or non-naturally in a particular cell, tissue or organism. This includes DNA and fragments thereof, RNA and fragments thereof, cDNAs and fragments thereof, expressed sequence tags, artificial sequences including randomized artificial sequences.

Plant or Plant entity: refers to a whole plant or a part of a plant comprising, for example, a cell of a plant, a tissue of a plant, an explant, or seeds of a plant. This term further contemplates a plant in the form of a suspension culture or a tissue culture including, but not limited to, a culture of calli, protoplasts, embryos, organs, organelles, etc.

Polypeptide: means any chain of more than two amino acids, regardless of post-translational modification such as glycosylation or phosphorylation.

Promoter region: refers to a nucleotide sequence involved in the regulation of a specific gene. It is usually located at a 5' position of the transcriptional start site. Typically, the promoter region includes the TATA box and all regulatory elements (e.g. a silencing element which negatively regulates expression of the gene for proper regulation of a specific gene.

Resistant or Tolerant. By resistant is meant a cell or organism (such as a plant) which exhibits substantially no phenotypic changes as a consequence of an aggression by a pathogen (e.g. virus, fungus, insect, etc). By "tolerant" is meant a cell or organism which, although it may exhibit some phenotypic changes as a consequence of aggression by a pathogen, does not have a substantially decreased reproductive capacity or substantially altered metabolism.

SEBF nucleic acid: means any nucleic acid (see above) encoding a plant polypeptide that is capable, among other things, of mediating repression of a silencing element involves in plant defense mechanisms and capable of binding specifically onto the sequence BTGTCNC or YTGTCNC, the plant polypeptide having at least 90%, preferably at least 95% and most preferably 100% identity or similarity to the amino acid sequence shown in SEQ. ID. NO:23. When referring to a plant SEBF nucleic acid, the nucleic acid set forth in SEQ. ID. NO: 21 encoding SEQ. ID. NO: 22 is more particularly concerned. SEBF protein or SEBF polypeptide: means a polypeptide, a fragment thereof, or a functional SEBF homologue encoded by a SEBF nucleic acid as described above.

Similarity/Complementarity: In the context of nucleic acid sequences, these terms mean a hybridizable similarity under low, alternatively and preferably medium and alternatively and most preferably high stringency conditions, as defined below.

Specifically binds: means an antibody that recognizes and binds a protein but that does not substantially recognize and bind other molecules in a sample, e.g., a biological sample, that naturally includes proteins.

Substantially identical: means a polypeptide or nucleic acid exhibiting at least 50, 55, 60, 65, 70, 75%, preferably 80 or 85%, more preferably 90, 95%, and most preferably 97 or 99% identity or similarity to a reference amino acid or nucleic acid sequence. For polypeptides, the length of comparison sequences will generally be at least 20 amino acids, preferably at least 25, 30 or 40 amino acids, more preferably at least 50 or 75 amino acids, and most preferably at least 100 amino acids. For nucleic acids, the length of comparison sequences will generally be at least 50 nucleotides, preferably at least 60 nucleotides, more preferably at least 75 nucleotides, and most preferably 100 nucleotides. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Owl 53705). This software program matches similar sequences by assigning degrees of similarity to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

Stringency: For the purpose of defining the level of stringency, reference can conveniently be made to Maniatis et al. (1982) at pages 387–389, and especially paragraph 11. A low stringency is defined herein as being in 4–6×SSC/1% (w/v) SDS at 37–45° C. for 2–3 hours. Depending on the source and concentration of nucleic acid involved in the hybridization, alternative conditions of stringency may be employed such as medium stringent conditions which are considered herein to be 1–4×SSC/0.5–1% (w/v) SDS at greater than or equal to 45° C. for 2–3 hours or high stringent conditions considered herein to be 0.1–1×SSC/0.1–1.0% SDS at greater than or equal to 60° C. for 1–3 hours.

Transformed or Transfected or Transgenic cell: Refers to introduction of an exogenous nucleic acid, typically a gene or gene regulatory sequence, into a whole plant or a part thereof. By "transformation" is meant any method for introducing foreign molecules into a cell. *Agrobacterium* transformation, PEG treatment, lipofection, calcium phosphate precipitation, electroporation, and ballistic transformation are just a few of the teachings which may be used.

Transgenic plant: any plant having a cell which includes a DNA sequence which has been inserted by artifice into the cell and becomes part of the genome of the plants which develops from that cell. Preferred transgenic plants are those transformed with an exogenous nucleic acid introduced into the genome of an individual plant cell using genetic engineering methods.

Vector: A self-replicating RNA or DNA molecule which can be used to transfer an RNA or DNA segment from one organism to another. Vectors are particularly useful for manipulating genetic constructs and different vectors may have properties particularly appropriate to express protein(s) in a recipient during cloning procedures and may comprise different selectable markers. Bacterial plasmids are commonly used vectors. Preferably, the vectors of the invention are capable of facilitating transfer of a nucleic acid into a plant cell and/or facilitating integration into a plant genome.

Vegetal Host: refers to a cell, tissue, organ or organism comprising chloroplasts and capable to perform photosynthesis. This term is intended to also include hosts which have been modified in order to accomplish these functions. Algae and plants are examples of a vegetal host.

Wound and stress inducible gene: a plant gene that is induced by wounding or by an abiotic stress such as ultraviolet light, drought, salinity.

B) General Overview of the Invention

The present inventors have now discovered that only nine nucleotides, i.e. the sequence GACTGTCAC (SEQ ID NO:26), are required for full activity of the silencing element (SE) of PR-10a gene.

The present inventors have also identified a nuclear factor (identified herein after as "SEBF"), that shows sequence specific binding to the sequence BTGTCNC (SEQ ID NO:23). Database searches revealed the presence of this binding sequence in the promoter of numerous PR genes.

The present inventors have also found that the sequence BTGTCNC shows high sequence similarity to the sequence of the auxin response element, strongly suggesting a role for this sequence and SEBF in the regulation of genes induced by the plant hormone auxin and its functional analogs. Furthermore, the inventors have demonstrated that SEBF can recognize and bind the sequence corresponding to the AuxRE of the GH3 gene of soybean.

The present inventors have also found that SEBF could be involved in the regulation of ethylene synthesis through the action of auxins since the SEBF binding element is present in the promoter of the ACC synthase gene, which is induced by auxins and encodes a key enzyme in the biosynthesis of ethylene, another plant hormone.

The present inventors have also proceed to a molecular characterization of SEBF. The SEBF protein was purified to homogeneity, partly chemically sequenced and a cDNA encoding SEBF was isolated and sequenced. The deduced amino acid sequence of SEBF shows a high degree of sequence similarity with chloroplast RNA binding proteins.

Subcellular partitioning of leaf cells demonstrates that SEBF is located in both chloroplasts and nuclei, suggesting functions in both cellular compartments.

Overexpression of recombinant SEBF in a transient expression system results in SE-dependent transcriptional repression of a PR-10a-uidA reporter fusion, confirming the role of SEBF as a transcriptional repressor.

Using a two-hybrid system in the yeast, the present inventors further identified proteins interacting with SEBF. Among those is Pti4, a transcription regulator of PR genes during the defense response induced by plant pathogens. Interestingly, Pti4 is known to interact with the enzyme nitrilase, an enzyme involved in the biosynthesis of auxins. Furthermore, Pti4 is a member of the ethylene response element binding proteins (EREBP) which are known to be involved in the plant responses to ethylene. In addition, SEBF was found to interact with the ERF domain of Pti4 in two hybrid studies. The ERF domain is of particular interest because it is conserved among all ethylene response factors.

The present inventors have also demonstrated that an SE element present in the promoter of the tobacco chitinase defense gene CHN50 is able to bind SEBF and that a mutation in this element that prevents binding of SEBF derepresses (unblock) transcription. This result is of particular interest because this promoter contains a GCC box, which is the binding site of Pti4, and is regulated by ethylene possibly through the binding of ethylene response factors such as Pti4.

C) Nucleic Acids Comprising Specific Binding Sequences

According to a first aspect of the invention, there is provided an isolated or purified nucleic acid comprising a binding sequence onto which proteinic nuclear factor(s) specifically binds. According to a preferred embodiment, the binding sequence according to the invention is BTGTCNC (SEQ ID NO:23), B corresponding to any nucleotide other than A (i.e. T, C or G), and N corresponding to A, T, C or G. More preferably, the binding sequence according to the invention is YTGTCNC (SEQ ID NO:24), Y corresponding to a pyrimidine (i.e. T or C). The exact binding sequence may vary depending on specific genes and organisms as exemplified herein after in Table 5.

According to a related aspect, there is provided there is provided an isolated or purified nucleic acid comprising a sequence that consists of a gene regulatory element comprising a nucleic acid sequence that is essential for the full activity of the silencing element (SE) of PR-10a. According to one preferred embodiment, the gene regulatory element consists of a silencing element and it comprises sequence BTGTCNC (SEQ ID NO:23), and more preferably sequence YTGTCNC (SEQ ID NO:24). According to another preferred embodiment, the plant is potato and the essential sequence silencing element (SE) of PR-10a is CTGTCAC (SEQ ID NO:25 or 47).

The invention also concerns a DNA construct comprising the gene regulatory element and/or the binding sequence described above, and genetically modified plants entities comprising the gene regulatory element, the binding sequence and/or the DNA construct. In a preferred embodiment, the regulatory element is operatively linked to an inducible promoter.

As it will be shown in the example hereinafter, the sequence BTGTCNC was found to be the specific binding sequence of a transcriptional repressor of the silencing element (SE) of PR-10a named SEBF. The sequence BTGTCNC it thus an important sequence involved in the modulation of the activity of genes incorporating this sequence into their promoter region.

Accordingly, the invention is also concerned with genetically modified vegetal hosts in which transcriptional activity of a gene associated with presence or absence of sequence BTGTCNC in a promoter region of this gene has been altered.

Therefore, a related aspect of the present invention concerns a method for altering gene expression in a plant. The method comprises the step of altering in the plant binding of a nuclear DNA-binding protein to sequence BTGTCNC. Although the nuclear DNA-binding protein preferably consists of SEBF. A person skilled in the art will however understand that SEBF is not the only proteinic nuclear factor that could bind to the sequence BTGTCNC since other proteinic nuclear factor(s) could also do so. A non-limitative list of preferred nuclear DNA-binding proteins includes proteins having at least 48% identity or similarity to SEBF and more particularly those given herein after in Table 6. The present invention also encompass sequences hybridizing under low, preferably medium and more preferably high stringency conditions to the nucleic acid sequence BTGTCNC or to its complementary sequence.

D) SEBF and Other Polypeptides Binding to the Sequence BTGTCNC

According to further aspect the invention, there is provided an isolated or purified nucleic acid molecule encoding a polypeptide that is capable of specifically binding the sequence BTGTCNC (SEQ ID NO:23), and more preferably the sequence YTGTCNC (SEQ ID NO:24). There is also provided an isolated or purified polypeptide that is capable of specifically binding the sequence BTGTCNC (SEQ ID NO:23), and more preferably the sequence YTGTCNC (SEQ ID NO:24).

The identity of the polypeptide as well as the binding sequence (see Table 5) may vary depending on organisms and on specific genes for which activity is to be modulated. According to a preferred embodiment, the polypeptide of the invention has an amino acid sequence at least 80 or 85%, more preferably at least 90 or 95% and even more preferably 97, 99 or 100% identical to the amino acid sequence shown in FIG. 5 (SEQ ID NO:22) and to functional homologues thereof. According to another embodiment, the polypeptide has an amino acid sequence encoded by a nucleic acid at least 80 or 85%, more preferably at least 90 or 95% and even more preferably 97, 99 or 100% identical to the nucleic acid sequence shown in FIG. 10 (SEQ ID NO:21), to its open reading frame (nucleotides 68 to 937), or to a fragment thereof. More preferably, the polypeptide of the invention is also capable of modulating the activity of genes incorporating the sequence BTGTCNC or YTGTCNC into their promoter region. A person skilled in the art should be capable, without undue experimentation of determining the exact nucleotide sequences coding for the polypeptide of the present invention.

According to a most preferred embodiment, the polypeptide of the invention is a transcriptional repressor called "SEBF". The sequence of the SEBF cDNA and predicted amino acid sequence is shown in FIG. 10 and in the "Sequence Listing" section. SEQ ID NO:21 corresponds to the potato SEBF cDNA and SEQ ID NO:22 corresponds to the predicted amino acid sequence of the protein.

The potato SEBF gene encodes a protein of 289 amino acids long. In silico analysis indicates that potato SEBF protein has the following features: it has a molecular weight of about 30 810 g/mol, an isoelectric point of about 4.6; an instability index of about 49; an aliphatic index of about 66.8; and a grand average of hydropathicity (GRAVY) of about −0.5. It further comprises many potential phosphorylation sites (18 Ser, 3 Thr, and 5 Tyr); and also 10 potential N-glycosylation sites. On an SDS PAGE under denaturing conditions, it has an apparent molecular weight, of about 28 to about 29 kDa. It also has the biological activity of a transcriptional repressor.

Blast searches were made to identify sequence identity SEBF and other existing sequences. Table 1 herein after provides a list of sequence showing similarity to SEBF (nucleotide vs nucleotide). Table 2 provides a list of proteins homologous to SEBF (protein vs protein) and Table 3 provides a list of predicted proteins showing similarities to SEBF (protein vs translated nucleotide).

The polypeptides and nucleic acid molecules of the present invention, and more particularly SEBF and/or is binding sequence, may be prepared by any suitable process. They may for instance be obtained by chemical synthesis when appropriate. They may also be prepared using biological processes involving cloning or expression vectors. Such vectors would comprise a polynucleotide sequence incorporating the nucleic acid molecule of interest such as and/or comprise a polynucleotide sequence encoding for the peptide of interest. Therefore, the present invention encompass such cloning or expression vectors and more particularly those encoding SEQ ID NO:22 and those comprising nucleotides 68 to 937 of SEQ ID NO:21. In addition, standard techniques, such as the polymerase chain reaction (PCR) and DNA hybridization, may be used to clone additional SEBF homologues in other plant species.

Therefore, in a related aspect, the invention is directed to a method for producing, in vitro, a polypeptide capable of specifically binding the sequence BTGTCNC (SEQ ID NO:23), and more preferably the sequence YTGTCNC (SEQ ID NO:24), and having preferably the biological activity of a transcriptional repressor. This method comprises the step of: 1) culturing in vitro, in a suitable culture medium, a cell incorporating an expression vector as described previously; and optionally 2) collecting in the culture medium polypeptides produced by these cells. Methods for producing such genetically modified cells and methods for using these cells in the production of proteins/peptides are well known in the art and will no be described in detail herein.

TABLE 1

Nucleotide sequence showing similarity to SEBF (nucleotide vs nucleotide)

| Sequence | NCBI acc. number | Identity raw | percent | Expect[1] |
|---|---|---|---|---|
| mRNA for cpRBP30, Tobacco | GI: 19707 | 777/885 | 87 | 0.00E+00 |
| mRNA for cp29A, Tobacco | GI: 19753 | 481/544 | 88 | 1.00E−54 |
| mRNA for cp31, Tobacco | GI: 19709 | 434/456 | 95 | 2.00E−58 |
| mRNA for cp29B, Tobacco | GI: 14134 | 345/380 | 91 | 1.00E−44 |
| At2g37220 gene, Arabidopsis | GI: 13877808 | 130/154 | 84 | 1.00E−22 |
| mRNA for cp29 (At3g53460), Arabidopsis | GI: 18409841 | 126/155 | 81 | 3.00E−11 |
| mRNA for 24 kDa RBP, Spinach | GI: 1015369 | 93/107 | 87 | 9.00E−05 |

[1]The expect value represents the possibility of choosing a particular sequence randomly

TABLE 2

Proteins similar to SEBF

| Protein | NCBI acc. number | Identity raw | percent | Similarity raw | % | Expect[1] |
|---|---|---|---|---|---|---|
| cp29A, Tobacco | GI: 12230584 | 191/230 | 83 | 198/230 | 86 | 1.00E−118 |
| 30 kDa ribonucleoprotein, Tobacco | GI: 1350820 | 186/232 | 80 | 193/232 | 83 | 4.00E−88 |
| cp29B, Tobacco | GI: 12230585 | 173/245 | 70 | 188/245 | 76 | 3.00E−83 |
| 31 kDa ribonucleoprotein, Tobacco | GI: 1350821 | 172/245 | 70 | 189/245 | 76 | 2.00E−73 |
| Putative RNA binding protein, Arabidopsis | GI: 15228102 | 148/219 | 67 | 173/219 | 78 | 2.00E−73 |
| Putative RNA binding protein, Rice | GI: 18921322 | 137/221 | 61 | 166/221 | 74 | 8.00E−68 |
| RNA binding protein, Spinach | GI: 7446360 | 142/224 | 63 | 162/224 | 71 | 1.00E−60 |
| cp29, Arabidopsis | GI: 681904 | 144/265 | 54 | 167/265 | 62 | 2.00E−59 |
| RNA binding protein, Avocado | GI: 19032260 | 113/225 | 50 | 147/225 | 65 | 2.00E−48 |
| cp31, Arabidopsis | GI: 1076305 | 112/226 | 49 | 146/226 | 64 | 3.00E−48 |
| RNP-D, Arabidopsis | GI: 629557 | 112/222 | 50 | 144/222 | 64 | 5.00E−47 |
| RNP-T, Arabidopsis | GI: 15233980 | 112/222 | 50 | 144/222 | 64 | 1.00E−46 |
| 28 kDa ribonucleoprotein, Tobacco | GI: 133246 | 102/219 | 46 | 142/219 | 64 | 1.00E−46 |
| RNA binding protein, Pea | GI: 7446357 | 110/213 | 51 | 138/213 | 64 | 2.00E−46 |

TABLE 2-continued

Proteins similar to SEBF

| Protein | NCBI acc. number | Identity raw | Identity percent | Similarity raw | Similarity % | Expect[1] |
|---|---|---|---|---|---|---|
| RNA binding protein 2, *Arabidopsis* | GI: 475719 | 112/222 | 50 | 144/222 | 64 | 2.00E−46 |
| cp31, Barley | GI: 7446358 | 114/220 | 51 | 145/220 | 65 | 6.00E−46 |
| Ps16, Wheat | GI: 7446356 | 113/221 | 51 | 146/221 | 65 | 5.00E−45 |
| DNA binding protein, *Arabidopsis* | GI: 99684 | 112/222 | 50 | 144/222 | 64 | 9.00E−45 |
| RNA binding protein, Ice plant | GI: 1076251 | 112/228 | 49 | 140/228 | 61 | 2.00E−44 |
| RNA protein-like, *Arabidopsis* | GI: 15240641 | 110/225 | 48 | 141/225 | 61 | 5.00E−44 |
| 28 kDa ribonucleoprotein, Spinach | GI: 133247 | 116/217 | 53 | 140/217 | 64 | 1.00E−43 |
| nucleic acid-binding protein, Maize | GI: 100903 | 112/221 | 50 | 143/221 | 64 | 7.00E−42 |
| CEBP-1, Clove pink | GI: 7446355 | 107/245 | 43 | 140/245 | 56 | 5.00E−41 |
| RNA binding protein 3, *Arabidopsis* | GI: 475720 | 93/172 | 54 | 117/172 | 67 | 3.00E−40 |
| RNP1, Kidney bean | GI: 1076509 | 89/222 | 40 | 128/222 | 57 | 1.00E−34 |
| cp33, *Arabidopsis* | GI: 681912 | 87/222 | 39 | 138/222 | 61 | 1.00E−34 |
| ribosomal protein CEP52, *Arabidopsis* | GI: 17064758 | 87/222 | 39 | 137/222 | 61 | 3.00E−34 |
| cp33, Tobacco | GI: 133249 | 90/228 | 39 | 140/228 | 60 | 3.00E−34 |
| cp33, Barley | GI: 7446339 | 89/226 | 39 | 130/226 | 57 | 1.00E−33 |
| RNA binding protein, Fava bean | GI: 7446361 | 87/226 | 38 | 132/226 | 57 | 2.00E−32 |
| Ribosomal protein 2, Spinach | GI: 7578881 | 76/203 | 37 | 118/203 | 57 | 3.00E−27 |
| NSR1, Yeast | GI: 253181 | 60/188 | 31 | 103/188 | 53 | 6.00E−21 |

[1]The expect value represents the possibility of choosing a particular sequence randomly

TABLE 3

Predicted proteins showing similarity to SEBF (protein vs translated nucleotide)

| Protein | NCBI acc. number | Identity raw | Identity percent | Similarity raw | Similarity percent | Expect[1] |
|---|---|---|---|---|---|---|
| mRNA for cpRBP30, Tobacco | GI: 19707 | 210/293 | 71 | 220/293 | 74 | 1.00E−102 |
| mRNA for cp29A, Tobacco | GI: 19753 | 208/292 | 71 | 216/292 | 73 | 1.00E−101 |
| mRNA for cp31, Tobacco | GI: 19709 | 173/254 | 68 | 191/254 | 75 | 3.00E−181 |
| At2g37220, *Arabidopsis* | GI: 16323481 | 152/248 | 61 | 181/248 | 72 | 2.00E−76 |
| mRNA for cp29 (At353460), *Arabidopsis* | GI: 681903 | 151/282 | 53 | 173/282 | 60 | 6.00E−68 |
| mRNA for PCO130298, Maize | GI: 21206992 | 134/203 | 66 | 159/203 | 78 | 1.00E−67 |
| mRNA for PCO127552, Maize | GI: 21208658 | 129/192 | 67 | 153/192 | 79 | 3.00E−65 |
| mRNA for 24 kDa RBP, Spinach | GI: 1015369 | 133/193 | 68 | 148/193 | 75 | 5.00E−63 |
| mRNA for cp31AHv, Barley | GI: 3550466 | 106/191 | 55 | 135/191 | 70 | 1.00E−48 |
| mRNA for cp31, *Arabidopsis* | GI: 681907 | 104/192 | 54 | 132/192 | 68 | 5.00E−48 |
| mRNA for RNP-T, *Arabidopsis* | GI: 18416422 | 104/192 | 54 | 132/192 | 68 | 5.00E−48 |
| mRNA for Ps16, Wheat | GI: 2443389 | 105/191 | 54 | 134/191 | 69 | 5.00E−48 |
| mRNA for rbp33, Avocado | GI: 19032259 | 103/192 | 53 | 132/192 | 68 | 2.00E−47 |
| mRNA for ribonucleoprotein, Pea | GI: 2330646 | 106/195 | 54 | 130/195 | 66 | 6.00E−47 |
| mRNA for CL2457_1, Maize | GI: 21216451 | 103/189 | 54 | 132/189 | 69 | 4.00E−46 |
| mRNA for cp28, Tobacco | GI: 19749 | 96/199 | 48 | 131/199 | 65 | 2.00E−45 |

[1]The expect value represents the possibility of choosing a particular sequence randomly E) SEBF Antibodies The polypeptides and polynucleotides of the invention may also be used for producing polyclonal or monoclonal antibodies capable of recognizing and binding the same. Accordingly, the invention also features a purified antibody (monoclonal or polyclonal) that specifically binds to a SEBF protein and/or a functional homologue thereof, such as SEBF homologous proteins in other plants species.

The Exemplification section of the application describes the preparation of a SEBF antibody. This antibody was also tested against a tobacco leaf extract and two strong bands of 28 and 29 kDa (probably corresponding to cp29A and cp29B respectively) were revealed. A preliminary test also suggests that the antibody the prepared SEBF antibody also recognises homologous proteins in *Arabidopsis thaliana.*

The antibodies of the invention may be prepared by a variety of methods using the SEBF proteins or polypeptides described above. For example, the SEBF polypeptide, or fragments thereof, may be administered to an animal in order to induce the production of polyclonal antibodies. Alternatively, antibodies used as described herein may be monoclonal antibodies, which are prepared using hybridoma technology (see, e.g., Hammerling et al., In Monoclonal Antibodies and T-Cell Hybridomas, Elsevier, N.Y., 1981).

SEBF antibodies may be used for preventing the action of SEBF in the plant. For example, a transgenic plant could be made which expresses an SEBF antibody (ex a single-chain antibody). Binding of this antibody to SEBF would inhibit its activity, therefore leading to derepression of genes under the control of SEBF. Accordingly, preferred antibodies are "neutralizing" antibodies. By "neutralizing" antibodies is meant antibodies that interfere with any of the biological activities of the SEBF polypeptide, particularly the ability of SEBF to repress gene activity. The neutralizing antibody may reduce the ability of SEBF polypeptides by preferably 50, 55, 60 or 65%, more preferably by 70, 75, 80 or 85%, and most preferably by 90, 95, 99% or more. Any standard assay, including those described herein, may be used to assess potentially neutralizing antibodies. Once produced, monoclonal and polyclonal antibodies are preferably tested for specific SEBF recognition by Western blot, immunoprecipitation analysis or any other suitable method.

Alternatively, the antibody could be specifically targeted to the plastids by translational fusion with a plastid transit peptide, therefore leading specifically to inhibition of plastidic functions of SEBF. Time of expression of the antibody could be controlled by placing its expression under the control of an inducible promoter, such as a promoter inducible by treatment with estrogens. The present invention therefore encompass such antibodies and methods for using the same. Methods for producing antibodies are well known in the art.

F) Genetically Modified Cells and Plants

The invention is also concerned with vegetal hosts, particularly plants, genetically modified for reducing (or increasing) the regular biological activity associated with the presence (or absence) into the regulatory/promoter region of the genes of the plant, of the sequence BTGTCNC (SEQ ID NO:23), and more preferably the sequence YTGTCNC (SEQ ID NO:24). Depending on specific uses as it will be described hereinafter, it may be advantageous to have plants in which at least some cells have been genetically modified so that the sequence BTGTCNC is inactive (mutation, deletion, etc). In other cases, it may be preferable to insert the sequence BTGTCNC or YTGTCNC into specific genes of the plants.

The invention is also concerned with cells and organisms genetically modified for expressing higher (or lower) levels of polypeptide(s) that is capable of specifically binding the sequence BTGTCNC (SEQ ID NO:23), and more preferably the sequence YTGTCNC (SEQ ID NO:24) (i.e. modulation of the cells or organisms endogenous levels). Depending of specific uses as it will be described hereinafter, it may be advantageous to have cells, and more particularly plant cells, that have been genetically modified to increase the levels of at least one polypeptide capable of specifically binding the sequence BTGTCNC or YTGTCNC, such as the SEBF protein or of a functional SEBF homologue. In other cases, it may be preferable to reduce the levels of such polypeptide(s).

Specific examples on how to prepared and/or used such genetically modified plants are described in Section H.

G) Compositions

The invention also relates to compositions for 1) modulating in plants the regular biological activity associated with the presence (or absence) of the sequence BTGTCNC (SEQ ID NO:23), and more preferably the sequence YTGTCNC (SEQ ID NO:24) and/or 2) modulating in plants the levels of expression of the polypeptide(s) capable of specifically binding the sequence BTGTCNC (SEQ ID NO:23), and more preferably the sequence YTGTCNC (SEQ ID NO:24) (i.e. modulation of the plant endogenous levels).

Such a composition would comprise an effective amount of at least one compound that is capable of, directly or indirectly, achieving one or both of the above mentioned desired effect, in combination with a diluent or a carrier. Herbicides are example of small molecules that affect plant physiology and development by binding and inhibiting the function of specific plant proteins. The compound(s) and its amount would be selected such that, following application of the composition of the invention, the desired modulation occurs into at least some of the cells of the plant when compared to a corresponding plant in the absence of the composition. More specific but non restrictive examples of suitable compositions according to the invention will be given hereinafter in Section H.

Plants treated with suitable compositions could show induced resistance to pathogens. Depending on time of treatment, the compositions could also be used to increase fruit maturation and number, or to induce senescence.

The carrier or diluent can be a solvent such as water, oil or alcohol. The composition may also comprise others active agents such as fertilizers and growth regulators. The inducing composition may also be formulated with emulsifying agents in the presence or absence of fungicides or insecticides, if required. The precise amount of compound employed in the practice of the present invention will depend upon the type of response desired, the formulation used and the type of plant treated.

H) Specific Examples of the Uses of the Invention

The following examples are illustrative of the wide range of applicability of the present invention and are not intended to limit its scope.

I-Increase Plant Resistance or Tolerance to Pathogens

Since SEBF is a transcriptional repressor of the defense response, and that its binding site has been found in numerous defense genes whose expression has been shown to lead or correlate to the defense response in plants, inhibition or reduction of SEBF accumulation (and/or of a functional SEBF homologue) and/or inhibition or reduction of the regular protein biological activity could increase the plant resistance to pathogens or to a faster induction of its defense mechanisms.

Such reduction of SEBF endogenous levels and/or reduction of SEBF biological activity (and/or levels or activity of a functional SEBF homologue) could be achieved in all plant species, by a number of means, including: expression in a transgenic plant of an antisense copy of the SEBF gene, or part of the gene; by expression of a sense copy that induces a co-suppression mechanism of SEBF; by production of a knock out of the SEBF gene by inserting therein a foreign DNA molecule; by chemical mutagenesis of the SEBF gene; by expression of a ribozyme cleaving SEBF mRNA; or by any other mean leading to the reduction of SEBF gene expression, accumulation of SEBF mRNA, and other suitable methods.

Similarly, SEBF binding site could also be genetically modified so that the sequence BTGTCNC (or YTGTCNC) becomes inactive (removal, mutation, deletion, etc).

Addition of the sequence BTGTCNC (or YTGTCNC) into the promoter of a gene of interest would reduce the level of expression of this specific gene. In some cases, for instance where the endogenous SEBF activity would be too weak, overexpression of SEBF could be required, in addition to the insertion of the SE sequence, for proper gene control under SE. On the other hand, removal of the sequence BTGTCNC (or YTGTCNC) would give higher sequence of expression. Such promoter alterations would be useful in plants where the level of SEBF (and/or functional SEBF homologue) cannot be altered. For example, removal of this sequence from a defense gene and the introduction of this modified gene in transgenic plants would lead to constitutive expression of this gene and to higher resistance to pathogens.

Overexpression of SEBF (and/or of a functional SEBF homologue) could lead to plants with reduced resistance to infection. This property could also be useful to control transgenic plants dissemination. For example, a transgenic plant engineered to express medicinal compounds could be further genetically modified so that it becomes hypersensitive to pathogens. This would allow easy elimination of these plants in cultivated fields by treatment of these plants with a pathogen known not to infect wild type plants.

II. Modifying Plant Responses to Auxins and Ethylene i) Auxins

Auxins are diffusible growth-promoting plant hormones. The primary auxin present in most plant is indole-3-acetic acid (IAA). It is active in low concentrations and synthetic analogs, 2,4-dichlorophenoxyacetic acid (2,4-D) and naphtalene-1-acetic acid (NAA), are used in agriculture to induce rooting and to promote the set and development of fruit. At high concentrations auxins inhibit plant growth and are often used as herbicides. Indole-3-acetic acid is synthesized mainly from L-tryptophan but an alternative route involves the conversion of indole-3-acetonitrile through the action of nitrilases. High concentrations of auxins are generally accompanied by an increased rate of ethylene biosynthesis due to the activation by auxins of the ACC synthase gene, which controls the production of ethylene.

As it will be shown in Example 1 hereinafter, the auxin response element overlaps with that of SEBF. This suggest that SEBF (and/or functional SEBF homologues) is able to bind to the auxin response element. Therefore SEBF and its functional homologues may be involved in the repression of genes controlled by auxin. Therefore, induction of genes controlled by auxins could be increased or decreased by modulating the endogenous levels of SEBF (and/or levels of functional SEBF homologues). SEBF levels could be decreased by one of the strategy described in Section I hereinabove. Plants with lower levels of SEBF or with a lower SEBF activity could have an increased sensitivity to endogenous auxins and exhibit an increased growth, rooting and fruit number as compared to other plants, and vice versa.

Plants with lower endogenous levels of SEBF (and/or functional SEBF homologues) or with a lower SEBF activity could also become more sensitive to exogenous treatment with auxin and its analogs. Therefore less of auxin-based herbicides could be used to eliminate these plants as compared to other plants. This property could also be useful to control transgenic plants dissemination. For example, a transgenic plant engineered to express medicinal compounds could be further genetically modified so that it becomes hypersensitive to auxinic herbicides. This would allow easy elimination of these plants in cultivated fields by spraying with low doses of the auxinic herbicide. Alternatively, plants with higher endogenous levels of SEBF such as transgenic plants over-expressing the SEBF gene could be less sensitive to auxin and analogs thereof, thereby conferring auxinic herbicide resistance to these plants.

Of course, insertion, deletion, mutation, of SEBF binding site sequence could also be considered to increase/decrease SEBF biological activity and modulate accordingly plants auxinic response.

ii) Ethylene

Ethylene influences seed germination, root and shoot growth, flower development, senescence and abscission of flowers and leaves, and fruit ripening. Ethylene is what causes fruits to over ripen and this is the major cause of fruit decay after harvest. ACC synthase, which is induced by auxins, catalyses the rate limiting step in ethylene biosynthesis.

As it will be shown in Example 1 hereinafter, the SEBF binding site is present in the promoter of the ACC synthase gene in potato and in numerous plant species (see Table 5). This strongly suggests that the auxin induction of the ACC synthase gene is regulated by SEBF. This hypothesis is also supported, as it will be shown in the example hereinafter, by the interaction of SEBF with Pti4, a member of the ethylene response element binding proteins family.

Plants with higher endogenous levels of SEBF (and/or of a functional SEBF homologue), such as transgenic plants over-expressing SEBF, should therefore be capable of down regulating ACC synthase and be capable of reducing the production of ethylene. Reduction of ethylene production would in turn delay fruit ripening and protect fruits against over-ripening.

On the other hand, plants with lower endogenous levels of SEBF or lower SEBF activity such as plants expressing an antisense copy of the SEBF gene, or part of it, could exhibit an early fruit maturation.

Addition of the sequence BTGTCNC (or YTGTCNC) into the promoter of a gene of interest would reduce the level of expression of this specific gene. On the other hand, removal of the sequence BTGTCNC (or YTGTCNC) would give higher sequence of expression. Such promoter alterations would be useful in plants where the level of SEBF cannot be altered. For example, removal of the BTGTCNC (or YTGTCNC) sequence from the promoter of the ACC synthase gene could lead to increase production of ethylene. After modification, the modified promoter and the coding sequence would be introduced in plants to create transgenic plants.

III. Chloroplastic Functions

Lowering the concentration of SEBF in the chloroplast or reducing SEBF biological activity in this organelle could result in marked phenotypic modifications of the plant. As it will be shown in Example 1 hereinafter, SEBF homologues have been shown to interact and stabilize RNA in plastids. Accordingly, it should be possible to modulate the expression of the plastid mRNAs onto which SEBF binds by modulating SEBF levels (and/or levels of functional SEBF homologues). This could give plants with a better photosynthetic or carbon fixation rate or plants better adapted to their environment.

IV. Protein Modules and Other Research Tools

As it will be shown in the example hereinafter, SEBF can be localized in two different compartments: the nucleus and the plastid. This indicates that SEBF amino acid sequence comprises a first "tag" (amino acids 1 to 59 of SEQ ID NO:22) which contains the localization information to direct SEBF to the plastid and a second "tag" to direct SEBF to the nucleus. Such tags could be used to direct other proteins to the plastid or nucleus by making a translational fusion between this tag(s) and the protein to be targeted into these cellular compartments.

Preliminary evidence also suggests that SEBF is released from its DNA binding element upon wounding or pathogen challenge of the plant. This feature could be used to create promoter systems tightly regulated in absence of inducing events. This could be achieved by inserting the SEBF binding sequence inside known inducible promoters. Such genetically modified promoters would then require two inducible events (one being the newly introduce SEBF binding sequence) in order to activate expression of a related gene.

V. Screening for Molecules Modulating SEBF Binding

Since SEBF is a binding molecule, this characteristic could be used for screening and/or identifying novel compounds that: inhibit the binding of SEBF to its DNA element (the sequence BTGTCNC); that inhibit the binding of SEBF to plastid or nuclear mRNAs; that inhibit the interaction of SEBF with another protein; and/or that negatively affect SEBF tridimensional structure (e.g. post-translational modifications).

Inhibition of SEBF binding activity could be measured in vitro by electromobility shift assays, by in situ by treating a plant with various chemicals, or by any other suitable method known in the art.

Compounds capable of inhibiting SEBF binding activity would have many uses as describe hereinbefore, and more particularly for increasing a plant resistance to pathogen or induce its defense response mechanism; for increasing a plant sensitivity to endogenous auxins and thereby increase growth, rooting and fruit number of the plant; increasing a plant sensitivity to auxin-based herbicides; and induce fruit maturation.

Similarly, compounds capable of increasing SEBF binding activity or would have many uses as described hereinbefore, and more particularly for reducing a plant sensitivity to auxin and analogs thereof (thereby conferring auxinic herbicide resistance to these plants); for delaying fruit ripening and protecting fruits against over-ripening caused by production of ethylene.

EXAMPLE 1

The following example is illustrative of the wide range of applicability of the present invention and is not intended to limit its scope. Modifications and variations can be made therein without departing from the spirit and scope of the invention. Although any methods and materials similar or equivalent to those described herein can be used in the practice for testing of the present invention, the preferred methods and materials are described.

a) Introduction

A variety of defense specific events are induced in plants in response to pathogen infection, including the production of reactive oxygen species, activation of G-proteins, reinforcement of the cell wall and the induction of signal transduction cascades leading to the transcriptional activation of defense genes (Dixon et al., 1994; Blumwald et al. 1998). Although key components of the signaling cascades are being discovered, few transcription factors have been identified that integrate these signals at the transcriptional level.

The well characterized PR genes induced by pathogen invasion provide excellent models to study transcriptional regulation of defense genes. PR genes are subdivided into 11 classes based on sequence similarity (Van Loon et al., 1994). The PR-10 gene family is subdivided into two groups and encodes small, acidic intracellular proteins of 15–18 kD (Osmark et al, 1997). Although Rnase activity has been demonstrated for PR-10 proteins, they do not possess any sequence similarity with classical Rnases (Moiseyev et al., 1994; Swoboda et al., 1996). In potato, three members of this family have been identified of which PR-10a is the best characterized.

Expression studies have identified cis-acting elements involved in PR-10a gene regulation. An elicitor response element (ERE) located between nucleotides −135 and −105 is essential and sufficient for elicitor induced gene expression (Matton et al, 1993; Després et al., 1995; Desveaux et al, 2000). PBF-2, a single-stranded DNA binding factor, appears to play a role in activation of PR-10a from the ERE (Després et al., 1995; Desveaux et al, 2000). Although the presence of the ERE is sufficient for PR-10a activation, removal of the silencing element (SE), located between −52 and −27, leads to further activation, suggesting that this element participates, with the ERE, in the regulation of PR-10a (Matton et al, 1993; Després et al., 1995).

In the present invention, we demonstrate, using transient expression studies, that only 9 nucleotides containing the sequence GACTGTCAC are required for full SE activity. We have also identified a nuclear factor (SEBF), that shows sequence specific binding to the sequence BTGTCNC. Database searches revealed the presence of this sequence in the promoter of numerous PR genes. This sequence also shows high sequence similarity to the sequence of the auxin response element, suggesting a role for this sequence and SEBF in the regulation of genes induced by the plant hormone auxin and its functional analogs. In particular, the SEBF element is present in the promoter of the ACC synthase gene, which is induced by auxins and encodes a key enzyme in the biosynthesis of ethylene, another plant hormone. Therefore SEBF could be involved in the regulation of ethylene synthesis through the action of auxins.

SEBF was purified to homogeneity from potato tubers and sequencing of the N-terminus of the protein led to the isolation of a cDNA encoding SEBF. The deduced amino acid sequence shows a high degree of sequence similarity with chloroplast RNA binding proteins. Subcellular partitioning of leaf cells demonstrates that SEBF is located in both chloroplasts and nuclei, suggesting functions in both cellular compartments. Overexpression of recombinant SEBF in a transient expression system results in SE-dependent transcriptional repression of a PR-10a-uidA reporter fusion, confirming the role of SEBF as a transcriptional repressor. Using the yeast two-hybrid system, we identified proteins interacting with SEBF. Among those is Pti4, a transcription regulator of PR genes during the defense response induced by plant pathogens. Pti4 is known to interact with the enzyme nitrilase, an enzyme involved in the biosynthesis of auxins. Furthermore, Pti4 is a member of the ethylene response element binding proteins (EREBP) which are known to be involved in the plant responses to ethylene.

b) Materials and Methods

All standard molecular biology procedures were done according to Sambrook et al. (1989).

Plant Material

Potato tubers (*Solanum tuberosum* cv. Kennebec) were obtained from the Quebec Ministry of Agriculture "Les Buissons" Research Station (Pointe-aux-Outardes, Canada). Tubers were stored in the dark at 4° C. and brought to room temperature 24 hr before use. Leaf mesophyll protoplasts were isolated from 4–5 weeks old potato plants grown in growth chambers as described by Magnien et al. (1980). Potato leafs were isolated from plants grown in an environmental growth chamber (Conviron, Winnipeg, Canada) under long day photoperiod conditions.

GUS Reporter Constructs and Analysis

The wild type (WT) construct was created by PCR amplification of the PR-10a promoter fragment of plasmid p-135 (Matton et al., 1993) using PCR oligo1 (GCCMGCTTTAGATAAAATGACACAAATGTCAAAAATGG; SEQ ID NO:27) and oligo2 (CCACCCGGGGATCCAGCTTTGMC; SEQ ID NO:28) to replace the XbaI site at position −135 by a HinDIII site. After digestion with HinDIII and BamHI, the fragment was inserted into pBI201. Mutant m1 was described previously (pLP9, Desveaux et al., 2000). Mutants m3, m4 and m5 were created by PCR using mutated oligonucleotides (FIG. 2A) and PCR oligo 2. The PCR fragments were cleaved with XbaI and BamHI and inserted into the wild type plasmid described above. For mutant m2, a HinDIII/NcoI PCR fragment was synthesized using oligo 1 and oligo 3 (CAGTCCATGGTTAAATCMC; SEQ ID NO:29). Then a NcoI/BamHI PCR fragment was synthesized using oligo 2 and oligo 4 (TAACCATGGACTGTCACTTG; SEQ ID NO:30). Ligation of these fragments into pBI201 cleaved with HinDIII and BamHI created mutant m2 (SEQ ID NO:2). The following primers were used to amplify the CHN50 promoter from tobacco: 5'-GCCGCMGTTTTCTGCAGTGTTTTTGCTC-3' (SEQ ID NO:31) and 5'-GGTTTGGATCCAGTAG-TAAAGTGGCGA-3' (SEQ ID NO:32). The amplified DNA was digested with PstI and BamHI and then inserted into the same sites of plasmid pBI201. Mutations in the promoter were done with the ExSitem PCR-based site-directed mutagenesis kit (Stratagene) using the oligonucleotides shown in FIG. 12C and oligonucleotide CHN50R 5'-ATGTCTACTCCTGCGCTCATT-3' (SEQ ID NO:33). Amplifications were carried out in a Whatman/Biometra Tgradient™ thermal cycler. All constructs were sequenced to ensure that no mutations were inserted by PCR. The transient expression system was previously described (Mafton et al., 1993). All values were corrected for the efficiency of electroporation using luciferase activity resulting from the coelectroporation of 1 µg of plasmid pWB216 (Barnes, 1990).

The coding sequence for the full length SEBF was inserted into pBI223D which contains a double CaMV $^{35}$S enhancer. For transrepression studies 5 µg of expression vector was added to the assays. The control vector expressed a human fusion protein containing FK506-binding protein (FKBP; Pelletier et al., 1998) under the same promoter.

Preparation of Extracts

Crude nuclear extracts were prepared as follows: 200 g of potato tubers or 75 g of leaves were homogenized in a blender at maximum speed for 1 min in 250 ml of cold NEBH (10 mM PIPES-KOH, pH 6.0, 1 M 2-methyl-2,4 pentanediol, 0.15 mM spermine, 0.5 mM spermidine, 10 mM $MgCl_2$, 14.3 mM P-mercaptoethanol, 0.1 mM PMSF). After decantation at 4° C. for 5 min, the homogenate was filtered through 5 layers of Miracloth™ under vacuum. The filtrate was centrifuged at 5,000 RPM for 5 min in a Sorval GSA rotor to pellet the nuclei. The supernatant served as the cytosolic fraction. Nuclei were washed three times in NP-40 buffer (10 mM MES-NaOH pH 6.0, 260 mM sucrose, 10 mM NaCl, 1 mM EDTA, 0.15 mM spermine, 0.5 mM spermidine, 14.3 mM P3-mercaptoethanol, 0.1% BSA and 1% NP40) to remove organelle and cytoskeleton contamination. The final pellet was resuspended in 5 ml of 200 mM NaCl SEBF binding buffer (SBB: 10 mM Tris-HCl, pH 7.5, 1 mM EDTA, 14.3 mM β-mercaptoethanol, variable NaCl concentrations). Nuclei were ruptured by sonication and the lysate centrifuged at 15,000 RPM for 45 minutes. The supernatant was either used immediately for SEBF purification or stored at −70° C. in 10% glycerol. In such conditions SEBF binding activity was stable for months. Chloroplasts were prepared by the method of Gegenheimer (1990).

Determination of Enzymatic Activities in Extracts

Chlorophyll content was measured according to Arnon (1949). Alkaline pyrophosphatase, nitrite reductase and alcohol dehydrogenase were measured according to Gross and ap Rees (1986), Hucklesby et al. (1972) and Smith and ap Rees (1979), respectively.

Electrophoretic Mobility Shift Assays (EMSA)

Protein extracts (in 200 mM NaCl SBB) were mixed with 20,000 CPM of $^{32}$P end-labeled probe. The binding reaction (40 µl) contained 100 ng of poly(dI-dC) to eliminate non-specific binding. The reaction was left on ice for 15 min. Electrophoretic separation of the complexes was achieved by loading the mixture on a 5.7% polyacrylamide gel prepared in Tris-glycine buffer (25 mM Tris, 195 mM glycine) and applying 200 V for 2.5 h at 4° C. The gel was exposed overnight to a Kodak X-omat AR film at −70° C.

Purification of SEBF from Nuclear Extracts

Crude nuclear extracts were loaded onto a 3 ml Q-sepharose™ FPLC™ (Amersham-Pharmacia Biotech) column equilibrated in 200 mM NaCl SBB. The column was washed with 10 volumes of 200 mM NaCl SBB followed by 15 volumes of 300 mM NaCl SBB. SEBF was eluted in 4 ml of 400 mM NaCl SBB. The eluate was then submitted to two rounds of affinity purification. The affinity beads were prepared by coupling a biotinylated WT SE oligonucleotide to streptavidin coated paramagnetic beads (Sigma) according to Desveaux et al. (2000). The beads were washed twice with 400 mM NaCl SBB prior to use. To 1 ml of eluate was added 20 µl of EDTA 500 mM pH 8.0, 10 µg of poly(dI-dC) and 5 µl of NP-40. The mixture was added to the affinity beads and left on ice for 15 min with sporadic mixing. After separation of the beads from the solution using a magnet, the beads were washed in 1 ml of 200 mM NaCl SBB followed by a 1 ml wash with 1 M NaCl SBB. SEBF was eluted from the beads by two subsequent 0.1 ml of 2 M NaCl SBB and incubated at 37° C. for 5 min. The eluate containing SEBF was desalted using Ultrafree 4™ centrifugal filter 10 K BioMax™ (Millipore, Bedford, USA). The equivalent of 1 kg of tubers was pooled and acetone precipitated. The pellet was resuspended in Laemmli solubilizing buffer (Laemmli 1970) and loaded on a 12% SDS-polyacrylamide gel. The proteins were transferred to a PVDF membrane (BIO-RAD) and stained with Coomassie blue. Bands were cut and sent for N-terminal analysis at the Eastern Quebec Proteomics Core Facility (Ste-Foy, Canada). The sequence VTLSDFD-QIEEVEAGDDDEEEGGLSDEAGASYEERN?NPDL; SEQ ID NO:34) was obtained from amino terminal analysis of the 29 kD band. The southwestern analysis was done according to Vinson et al. (1988).

Cloning of SEBF

A degenerate oligonucleotide (GTKACV-VYTITCIGATTTYGAYCA; SEQ ID NO:35) corresponding to the N-terminal sequence of SEBF and a cs-RBD specific primer (ARRTTWCCIACRMRATYTT; SEQ ID NO:36; Mieszczak et al., 1992) (I corresponding to an inosine) were used to generate a 141 bp genomic PCR fragment of SEBF. The specific primer GTTTGAGTGAT-GAAGGTGC (SEQ ID NO:37) was derived from the sequence of the 141 bp fragment and used to probe a potato cDNA bank (Matton and Brisson, 1989) using the method proposed by Israel (1993). Twenty-three pools of 18,000 phages were used in PCR reactions using the gene specific primer and the M13 universal primer. Two pools gave a PCR fragment of approximately 1,000 bp. These pools were further diluted and the procedure repeated until it was possible to isolate a single plaque. A positive clone was excised by using the ExAssistm system (Stratagene), according to the manufacturers instructions. The clone was sequenced on both strands with Thermosequenasem (Amerham-Pharmacia Biotech) in a cycle-sequencing reaction that was then processed on a LI-COR™ automated sequencer (LI-COR, Lincoln, USA). SEBF nucleotide and amino acids sequences (SEQ ID NOs:21 and 22) were published by the present inventors on Dec. 10, 2001 in GenBank™ under accession No. AF389431.

Southern Analysis and Genomic Analysis

Procedures for the extraction of genomic DNA and Southern blotting were as described by Ausubel et al. (2001). The following primers were designed according to the predicted position of the introns in the tobacco and *Arabidopsis* SEBF homologues (Ye et al., 1991; Ohta et al., 1995) and used for PCR analysis of the genomic DNA:

```
T: GCCGTTCTGTCTTCACAATTCTTTTGCTTC;    (SEQ ID NO:38)

U: CAACATCTCCAGCACGCTCAAAAAGCTCAG;    (SEQ ID NO:39)

V: CCTCTGCTTCTTCCTGTAAGCTTGTCATAG;    (SEQ ID NO:40)

W: CAGTTGAAGCCGCCTGTCAACAATTTAATG;    (SEQ ID NO:41)

X: TTGACGGGAGGGCACTGAGGGTGAATTCTG;    (SEQ ID NO:42)

Y: GCTTTCAATTGCAT-CGTTGACCTCCTTAG;    (SEQ ID NO:43)
and

Z: GCTTCAGCAGGACTTACACGGATGGCCCTG.    (SEQ ID NO:44)
```

Antibody Production and Western Blotting

The cDNA encoding SEBF was fused to the glutathione S-transferase (GST) gene in plasmid pGEX4T1™ (Amersham-Pharmacia Biotech). The fusion protein (GST-SEBF) was expressed in BL21 cells. After lysis of the cells the fusion protein was purified on a glutathione column (Smith and Johnson, 1988). The GST tag was cleaved with thrombin (Amersham-Pharmacia Biotech) and removed from the extract by a second pass on the glutathione column. Rabbit immunization was done according to Harlow and Lane (1988). Briefly, 50 µg of recombinant SEBF was used to immunize rabbits followed by a second injection of 150 µg 30 days later to boost the immunological reaction. The rabbits were sacrificed fourteen days following the second injection. For western blot studies the SEBF antisera was used at a dilution 1:5000 and the antibody-antigen interaction was revealed with the ECL™ detection kit (Amersham Parmacia Biotech) according to manufacturers instructions.

Yeast Two-hybrid Screening

The two-hybrid screening was done using the DupLEX-A™ yeast two hybrid system (OriGene, Rockville, Md., USA). The coding sequence for mature SEBF was inserted in frame with the LEX-A DNA binding domain in the bait vector pEG202. A tomato cDNA library made in the target vector pJG4–5 was obtained from B. Baker at the U.S. Department of Agriculture (Zhang et al., 1999). Five million clones were screened in strain EGY48 according to the manufacturers instructions. Each positive clone was retransformed to verify the authenticity of the interaction. The positive clones were then sequenced on both strands using the T7 sequencing kit (Amersham-Pharmacia Biotech). Translated proteins were identified through the BLASTX™ program at NCBI™.

c) Results

Identification of SEBF

Previous studies identified a negative regulatory sequence (SE) in the promoter of the potato PR-10a gene (Matton et al., 1993; Després et al., 1995). We therefore sought to identify a nuclear protein able to regulate PR-10a expression through binding to this sequence. Since PR-10a appears to be positively regulated at the ERE by a single-stranded DNA (ssDNA) binding protein (Desveaux et al., 2000), we searched for proteins that could bind either single- or double-stranded forms of the SE. A crude nuclear extract of potato tubers was incubated with single- or double-stranded radiolabeled SE and analyzed by electrophoretic mobility shift assay (EMSA). FIG. 1 demonstrates that a nuclear factor, called SEBF for SE binding factor, bound the coding strand of the SE (lane 1). SEBF was not able to bind the non-coding strand (lane 3) or double-stranded DNA (lanes 4 through 6). These results show that SEBF is a ssDNA binding protein that recognizes only one strand of the silencing element.

We have previously demonstrated that another cis-element of the PR-10a promoter also interacts with a ssDNA binding protein. This element, located between –135 and –105, interacts with the ssDNA binding factor PBF-2 (Després et al., 1995; Desveaux et al., 2000), which has been shown to activate the transcription of a PR-10a-uidA reporter gene construct in protoplasts (Desveaux and Brisson, in preparation). Therefore, our data suggest that a large region of the PR-10a promoter is contacted by ssDNA binding proteins. A similar situation has been reported for several genes in animals (reviewed by Rothman-Denes et al., 1998) and is illustrated by the promoter of the c-myc proto-oncogene, where several classes of single-stranded cis elements occur in vivo and are bound by various specific ssDNA binding factors (Michelotti et al., 1996).

Binding of SEBF to the SE Correlates with the Transcriptional Repression of PR-10a A mutational analysis of the SE was performed to determine which nucleotides compose the SEBF binding site and whether these nucleotides are important in vivo for the regulation of PR-10a expression. Mutated forms of the SE coding strand were synthesized (FIG. 2A) and used as probes in EMSA studies (FIG. 2B). The same mutations were also introduced into the PR-10a promoter fused to the uidA reporter gene encoding β-glucuronidase (GUS) and the resulting transcriptional activity was measured in a transient expression system (FIG. 2D). As shown in FIG. 2B, binding of SEBF to mutants m3 (SEQ ID NO:3) and m4 (SEQ ID NO:4) was significantly reduced compared to WT (SEQ ID NO:45). In contrast, introduction of these mutations in the promoter of PR-10a led to an increased activity of the reporter gene in transient studies (FIG. 2D, m3 and m4). Mutations that showed either a slight increase (FIG. 2B, m2 (SEQ ID NO:2)) or decrease (FIG. 2B, m5 (SEQ ID NO:5)) in binding did not show altered transcriptional activities (FIG. 2D, m2 and m5). Binding of SEBF was completely abolished using mutant m1 (SEQ ID NO:1), where 80 percent of the sequence has been changed (FIG. 2B, m1). This absence of binding correlated with the highest transcriptional activity observed in transient studies (FIG. 2D, m1). Therefore, the transcriptional activity of the PR-10a promoter is inversely correlated to the in vitro binding of SEBF at the SE. This suggests that SEBF is the trans-acting factor responsible for SE-mediated repression of PR-10a.

The Sequence BTGTCNC Defines the DNA Binding Site of SEBF

Figure 2:
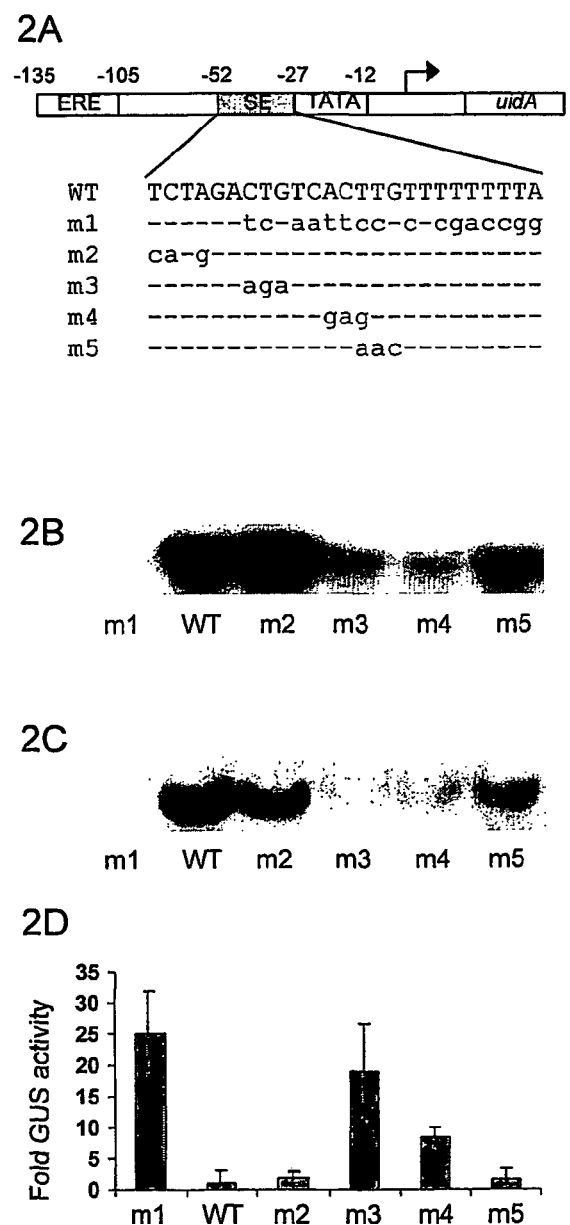
FIGS. 2A, 2B, 2C and 2D show mutational analysis of potato silencing element (SE).

Results presented in FIG. 2 indicate that the SEBF binding site is located within the sequence GACTGTCAC (SEQ ID NO:26). To further delineate this element, additional mutations were introduced into this region and their effect on SEBF binding was monitored by EMSA. As indicated in FIG. 3, mutations affecting the sequence CTGTCAC (SEQ ID NO:25) dramatically reduced the binding of SEBF (FIGS. 3B and 3C, mutants m8 (SEQ ID NO:8), m9 (SEQ ID NO:8), m11 (SEQ ID NO:11), m13 (SEQ ID NO:13), m14 (SEQ ID NO:14), m15 (SEQ ID NO:15), m16 (SEQ ID NO:16), m17 (SEQ ID NO:17), m18 (SEQ ID NO:18)), whereas mutations outside this region did not affect binding (FIGS. 3B and 3C mutants m6 (SEQ ID NO:6), m7 (SEQ ID NO:7), m12 (SEQ ID NO:12), m20 (SEQ ID NO:20)). Mutations of the only A in this sequence did not affect binding (FIGS. 3B and 3C; mutants m12 (SEQ ID NO:12) and m19 (SEQ ID NO:19)). In fact, any nucleotides could substitute the A without affecting SEBF binding (not shown). Further analysis of the SEBF binding site revealed that the first C could be substituted by G or T. The only nucleotide that reduces SEBF binding at that specific position is A (FIG. 3, m13 (SEQ ID NO:13)). Therefore, the consensus SEBF binding site is BTGTCNC (SEQ ID NO:23), preferably YTGTCNC (SEQ ID NO:24), where N is all nucleotides, B is C, G or T, and Y is C or T.

The SEBF Binding Bite is Present in Other Defense Genes

Table 5 present the results of a DNA database searches reveal that the SEBF binding site is present in the promoter of a number of genes known to be induced by pathogens. These include: glucanases from tomato and rice (GenBank™ acc. Nos AF077340 and X58877); chitinases from Arabidopsis, bermudagrass, potato, rice and tobacco (GenBank™ acc. Nos Y14590, AF105426, AF153195, AF013581, X16938); PR-1 from barley and tobacco (GenBank™ acc. Nos Z48728 and X66942) and PR-10 from apple, birch, parsley and pea (GenBank™ acc. Nos AF020542, AJ289771, U48862 and U31669).

A previously identified repressor element of the CHN50 gene contains the SEBF binding site. This element was tested in EMSA to verify if it could be recognized by SEBF. FIGS. 9 and 12A demonstrate that SEBF can bind the repressor element of the CHN50 gene suggesting a role for SEBF in the regulation of this other defense genes. In addition, FIG. 12B demonstrates that the residues important for SEBF binding greatly contribute to the repression of the CHN50 gene. Furthermore, a mutation that abolishes SEBF binding (M2, FIG. 12A) results in derepression of the CHN50 gene (M2, FIG. 12B). Table 5 also shows that SEBF binding site is found in numerous wound or stress inducible genes. Altogether these results suggests an important role for SEBF and its element SEBF in plant defense responses and more particularly in the regulation of plant defense genes.

The SEBF Binding Site is Similar to AuxRE

Figure 11:
FIGS. 11A, 11B and 11C show the binding of SEBF to the AuxRE sequence present in the GH3 promoter of soybean.

As shown in Table 5, comparison of the SEBF binding site (BTGTCNC) with other regulatory elements reveals a strong similarity to the auxin response element (TGTCTC; SEQ ID NO:55) present in composite AuxRE. Analysis of the nucleotide 5' to the TGTCTC of published AuxRE revealed an enrichment in purines (C or T) suggesting that most AuxRE are likely to be bound by SEBF. Furthermore, AuxRE were shown to repress the action of a constitutive enhancer element in the absence of auxins (Ulmasov et al., 1995) and they appear to be occupied, regardless of the auxin status, by a yet unidentified factor that can interact with ARF factors (Ulmasov et al., 1999). SEBF most probably corresponds to this factor since: 1) it is present in the nucleus of leaves and tubers; 2) it functions as a transcriptional repressor (see below); and 3) it should bind to most Aux-RE, as exemplified by SEBF binding to one of the most characterized AuxRE which is the D4 element of the GH3 gene of soybean (FIG. 11; Ulmasov et al., 1995).

Auxin is also known to negatively regulate several defense genes (Grosset et al., 1989; Jouanneau et al., 1991). Recently, an Arabidopsis pleiotropic mutant was isolated which shows both increased susceptibility to pathogens and auxin insensitivity, demonstrating complex interactions between the pathways leading to these phenotypes (Mayda et al., 2000). These results, and the strong similarity between the SEBF binding site and the AuxRE, raise the possibility that SEBF could also be involved in hormonal control of gene expression.

Purification of SEBF

A cDNA for SEBF was cloned using information deduced from the amino acid sequence of the purified protein. SEBF was purified from tuber nuclei using a combination of anion exchange chromatography and affinity purification. Table 4 hereinbelow shows that a 20,700 fold purification of SEBF was achieved.

TABLE 4

Purification of SEBF from potato tubers

| Fraction | Total Protein (mg) | Total Activity[a] (pg DNA) | Specific Activity (pg DNA/mg) | Purification (fold) | Yield (%) |
|---|---|---|---|---|---|
| Crude nuclear | 112 | $3.3 \times 10^6$ | $2.9 \times 10^4$ | 1 | 100 |
| Q-Seph[b] | 1.15 | $3.0 \times 10^6$ | $2.6 \times 10^6$ | 90 | 91 |
| Aff.1[c] | $4.0 \times 10^{-3d}$ | $2.3 \times 10^6$ | $5.8 \times 10^8$ | 20,000 | 70 |
| Aff.2[e] | $3.5 \times 10^{-3d}$ | $2.1 \times 10^6$ | $6.0 \times 10^8$ | 20,700 | 64 |

[a]Total activity determined by measuring labeled probe bound by SEBF in EMSA and calculating total pg of DNA bound in each fraction
[b]Q-Seph., Q-Sepharose Fast-Flow ™ anion exchange chromatography
[c]Aff.1, First round of DNA affinity chromatography
[d]Estimated from stained gels
[e]Aff.2, Second round of DNA affinity chromatography The analysis of the chromatographic fractions by SDS-PAGE and Coomassie staining revealed two distinct bands of 29 and 28 kD in the most purified fraction (FIG. 4, lane 4). To determine which of these two bands possessed DNA-binding activity, proteins from the second affinity purification (Aff.2) were transferred to nitrocellulose and probed with the wild type SE oligonucleotide. Results indicate that the two purified proteins can interact independently with the silencing element (FIG. 4, lane 5). Both of these proteins were subjected to N-terminal sequence analysis.

Cloning of SEBF

A 40 amino acid sequence was obtained from N-terminal sequencing of the 29 kD protein. Amino-terminal sequencing of the 28 kD protein showed more than one amino acid at each cycle. However, a clear sequence similarity with that of the 29 kD protein could be observed, suggesting that the 28 kD band contained degraded forms of the 29 kD protein. Using the amino acid sequence obtained from the 29 kD protein, a PCR strategy was elaborated to clone a cDNA (see materials and methods). The sequence of SEBF cDNA (SEQ ID NO:21) is shown in FIG. 10 whereas its amino acid sequence (SEQ ID NO:22), derived from the cDNA clone, is presented in FIG. 10 and in FIG. 5. The 40 residues determined by N-terminal sequencing (shown in bold in FIG. 5) are preceded by a 59 amino acid sequence with the attributes of a transit peptide. An acidic region present in the N-terminal region of the mature protein precedes two consensus sequence type RNA-binding domains (cs-RBD, underlined in FIG. 5). These domains, also known as RNA recognition motifs (RRM), RNP consensus sequences (RNP-CS) or RNP motifs (Burd and Dreyfuss, 1994), are separated by a glycine rich region. As mention previously, database searches indicated a high degree of sequence similarity with a family of nuclear encoded chloroplast RNA binding proteins (see Tables 1 to 3 hereinbefore).

The presence of RNA binding domains in SEBF, and the multiple functions associated with this domain, suggests that SEBF could also play a role in RNA processing. Tobacco chloroplast homologues of SEBF have been shown to bind mRNA and intron-containing pre-tRNAs (Nakamura et al., 1999). They have also been shown to confer stability and ribonuclease protection to mRNA in the chloroplasts (Nakamura et al., 2001). In addition, RNA editing in chloroplasts, like mammalian nuclear editing, also involves the presence of hnRNPs (Lau et al., 1997; Hirose and Sugiura, 2001). Therefore, SEBF represents a single-stranded-DNA binding factor that could be involved in the regulation of transcription of nuclear genes and the control of gene expression in plastids by binding to RNA.

To confirm that the cDNA-encoded protein functionally corresponds to SEBF, the protein was expressed as a GST fusion in E. coli, purified, and tested for binding to the SE. FIG. 2C shows that the recombinant protein binds to SE oligonucleotides with binding specificity similar to native SEBF (FIG. 2B).

Cellular Distribution of SEBF

Figures 5, 6:
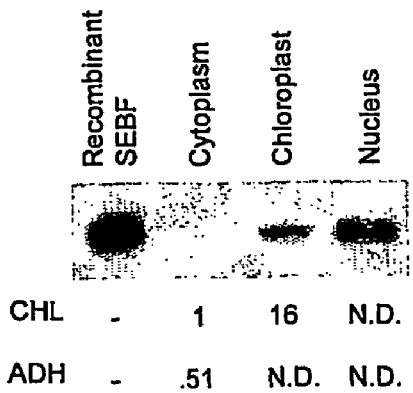
FIG. 5 shows the amino acid sequence of SEBF (SEQ ID NO:22; GenBank™ accession No AF38431). The predicted site for transit peptide cleavage is indicated by an arrow. The two consensus sequence type RNA binding domains (cs-RBD) are underlined. The amino acid sequence obtained through amino terminal sequencing is shown in bold characters.
FIG. 6 shows cellular localization of SEBF. Potato leaves were fractionated into cytoplasm, nuclei and chloroplasts. Ten µg of each fraction were separated by 12% SDS-PAGE. Proteins were transferred to nitrocellulose and the presence of SEBF was revealed using an anti-SEBF antibody. The first lane (10 ng of recombinant SEBF) shows the protein which served to immunize the rabbits. Chlorophyll (CHL) was used as a chloroplastic marker (data is presented as µg of chlorophyll [mg of protein]$^{-1}$) and alcohol dehydrogenase (ADH) as a cytoplasmic marker (data is presented as increased OD [mg of protein]$^{-1}$[min]$^{-1}$). N.D., not detectable.

The purification of SEBF from isolated nuclei (Table 4) indicates that SEBF is a nuclear protein. However, the presence of a putative transit sequence in recombinant SEBF suggests that the protein could also be present in plastids. This led us to investigate the subcellular localization of SEBF. Antibodies were raised against recombinant SEBF and subcellular fractions were obtained from potato leaves. The integrity of each fraction was verified by enzymatic assays. FIG. 6 shows that, as expected, alcohol dehydrogenase activity was restricted to the cytosolic fraction. The nuclei were free of the chloroplastic marker chlorophyll, and little contamination was observed in the cytosolic fraction. No detectable alkaline pyrophosphatase or nitrite reductase activities were found in nuclear preparation. These two enzymes are known to be located exclusively in the plastids (Miflin, 1974; Gross and ap Rees, 1986). Western blot analysis performed on these fractions revealed that a protein immunologically related to SEBF was present in chloroplasts and nuclei (FIG. 6). A single 29 kD band, corresponding to the molecular weight of the mature form of SEBF (FIG. 6, Recombinant SEBF), is present in both cellular compartments. No proteins of higher molecular weight were detected in any fraction, suggesting that if SEBF is synthesized as a precursor, it is efficiently processed by peptidases prior to nuclear import.

Dual Localization of SEBF

The presence of a similar sized, immunologically-related protein to SEBF in chloroplasts suggests that this protein is efficiently targeted to this cellular compartment. This is supported by the presence of a putative transit peptide encoded in the cDNA of SEBF and by studies in other species which have shown that SEBF homologues are present in the chloroplasts (Ye et al., 1991; Mieszczak et al., 1992; Ohta et al., 1995).

SEBF is a Single Copy Gene

To rule out the possibility that nuclear and chloroplastic SEBF could be the product of different genes, genomic DNA was digested with restriction enzymes and used for Southern blot analysis. As shown in FIG. 7A, probing the genomic DNA with an SEBF cDNA fragment resulted in a single EcoRI band and two HinDIII bands. These were the expected results for a single copy gene since no EcoRI sites and a single HinDIII site are found within the probe. The presence of two XbaI fragments is due to the presence of an XbaI site in the third intron of the gene (not shown). Analysis of potato genomic DNA by PCR led to the identification of three introns in the gene coding for SEBF (FIG. 7B). The introns are positioned between nucleotides 454 and 455, between nucleotides 556 and 557, and between nucleotides 869 and 870 of SEQ ID:21 for introns 1, 2 and 3 respectively. These three introns are present at the same position in homologues of SEBF in Arabidopsis and tobacco (Ye et al., 1991; Ohta et al., 1995). These results clearly indicate that there is only one copy of the SEBF gene in the potato genome. Since no introns are present in the 5' end of the gene (FIG. 7C), the absence of a transit peptide on the purified protein is not due to alternative splicing. This was confirmed by sequencing 5'RACE products which all showed sequences identical to that of SEBF (not shown). These results are also supported by the conservation of the genomic organization of this gene in tobacco and Arabidopsis.

Taken together, the results indicate that the nuclear-localized SEBF is encoded by a single-copy gene and that the transit peptide is not eliminated by differential splicing. This suggests that both the nuclear SEBF and the chloroplast protein are derived from the same precursor. As only the mature form of SEBF is detected in the nucleus, this also suggests that the precursor can be processed outside the chloroplast. Similar results were found in potato for the enzyme starch phosphorylase, which is synthesized as a precursor and targeted to the amyloplast in young tubers but accumulates in a processed form in the cytoplasm of older tubers (Brisson et al., 1989). In line with these data, Dahlin and Cline (1991) reported that import of proteins into plastids is developmentally regulated, with the plastids losing their ability to import precursors during maturation. This differential import of proteins could be controlled by phosphorylation of transit peptides, which has been shown to reduce chloroplast import rates (Waegemann and Soll, 1996). It will be interesting in the future to determine whether the subcellular localization of SEBF changes during development. Nonetheless, the dual localization of SEBF in chloroplasts and the nucleus makes this protein an ideal candidate for regulating metabolism in both subcellular compartments during the defense response. It is well established that, in addition to the activation of nuclear defense genes, infection leads to major changes in primary metabolism of the plant, including reductions in the rate of photosynthesis and synthesis of RuBisCO (Tang et al., 1996; Somssich and Hahlbrock, 1998). SEBF could therefore play a role in coordinating defense-induced changes in both compartments.

SEBF can Repress Transcription

The correlation between binding of SEBF to mutated forms of the SE and their activity as negative regulatory elements in protoplasts suggests that SEBF is the factor mediating SE dependent repression. This was confirmed by co-expressing SEBF and various reporter constructs in potato protoplasts. Although repression was observed using the wild type promoter construct, reporter activity was too low and the results were not statistically significant (FIG. 8, WT). This result was expected as promoter activity with the wild-type SE is already fully repressed. To circumvent this problem, we overexpressed SEBF in conjunction with a construction carrying the partially derepressed mutant m4 (see FIG. 2D), which is bound with less affinity than WT by recombinant and purified SEBF (FIGS. 2B an 2C). We expected that overexpression of SEBF would compensate for the lower binding affinity to this mutant. FIG. 8 demonstrates that indeed, a 68 percent decrease of promoter activity was attained when SEBF was overexpressed, compared to the activity observed with the overexpression of FKBP, a control protein (FIG. 8, m4). Repression was not seen when SEBF was overexpressed with mutant m1 (FIG. 8, m1), to which it does not bind, confirming that the repression observed requires a cis-element bound by SEBF and is not due to tethering of an activator or translational blocking. These results demonstrate that SEBF participates in SE mediated PR-10a repression and that expression of the SEBF precursor results in nuclear localized activity.

hnRNP are among the best characterized ssDNA binding proteins playing a role in the regulation of gene expression in eukaryotes. For example, hnRNP D and its homologues have been shown to activate (Tay et al., 1992; Tolnay et al., 2000; Lau et al., 2000) or repress transcription from a variety of promoters (Kamada and Miwa, 1992; Smidt et al., 1995; Chen et al., 1998). Another cs-RBD containing protein, human hnRNP A1, has been shown to repress transcription of the thymidine kinase gene (Lau et al., 2000). It is therefore not surprising that SEBF, a plant protein containing cs-RBDs, can act as a transcriptional repressor. Other plant proteins containing two cs-RBDs, such as *Arabidopsis* FMV-3b, carnation CEBP-1, and tobacco ACBF were also able to bind specific regulatory cis-elements (Didier and Klee, 1992; Maxson and Woodson, 1996; Séguin et al., 1997) and therefore represent potential transcriptional regulators.

SEBF Interacts with Pti4

The yeast two-hybrid system was used to determine to which proteins SEBF interacts. Of five interactors identified, two corresponded to SEBF, indicating that the protein is able to form multimers, one corresponded to a protein with similarity to a DEAD-box like RNA helicase (Itadani et al., 1994), and two interactors corresponding to the tomato transcription factor Pti4 (Zhou et al., 1997). Pti4 is known to interact with the Pto resistance gene which controls the defense response in tomato against bacterial pathogens. These results suggest that SEBF could be involved in the regulation of defense genes regulated by Pti4 and Pto.

With the two hybrid screen, other interactors (presented in Table 6) were also identified. SEBF could contribute to the regulation of these proteins and the processes involving these interactors.

TABLE 5

Occurrence of the SEBF binding site

| Gene | Organism | GenBank™ acc. No. | Sequence |
|---|---|---|---|
| Defense genes | | | |
| PR-10a | Potato | M29041 | CTGTCAC |
| PR-10b | Potato | M29042 | CTGTCAC |
| PR-10 (ypr10b) | Birch | AJ289770 | CTGTCTC |
| PR-10 (ypr10a) | Birch | AJ289771 | CTGTCAC |
| PR-10 | Apple | AF020542 | CTGTCAC |
| PR-10 | Parsley | U48862 | TTGTCTC |
| Chitinase | Tobacco | X51599 | ATGTCTC |
| Chitinase | Potato | AF153195 | TTGTCAC |
| Chitinase | Bermuda grass | AF105426 | TTGTCTC |
| Chitinase | *Arabidopsis* | Y14590 | TTGTCTC |
| Glucanase | Rice | X58877 | CTGTCAC |
| Glucanase | Tomato | AF077340 | CTGTCAC |

TABLE 5-continued

Occurrence of the SEBF binding site

| Gene | Organism | GenBank™ acc. No. | Sequence |
|---|---|---|---|
| PR-1 | Tobacco | X66942 | TTGTCAC |
| | | | CTGTCAC |
| PR-1 | Barley | Z48728 | TTGTCAC |
| Osmotin (PR-5) | Tobacco | S68111 | TTGTCAC |
| Osmotin (PR-5) | Tobacco | D76437 | GTGTCAC |
| Peroxidase | Wheat | X85230 | CTGTCAC |
| Alternative oxidase | Voodoo lily | Z15117 | CTGTCAC |
| Antifungal protein | *Gastrodia elata* | AF334813 | CTGTCTC |
| Ethylene production | | | |
| ACC synthase | Tomato | AF043122 | GTGTCAC |
| ACC synthase | Mungbean | AB018355 | CTGTCAC |
| ACC synthase | Potato 3 | Z27235 | TTGTCAC |
| | Potato 2 | Z27234 | ATGTCCC |
| | | | ATGTCTC |
| | Potato 1 | Z27233 | TTGTCCC (2x) |
| | | | TTGTCTC |
| | | | GTGTCAC |
| | | | ATGTCTC |
| ACC oxidase | Banana | AF030411 | TTGTCTC |
| Cellulase ethylene induced | Soybean | U34754 | CTGTCTC |
| Wound and stress induced | | | |
| myrosinase-associated protein | *B. napus* | AJ223307 | CTGTCAC |
| wun-1 | Sweet potato | X17554 | CTGTCAC |
| osr40g2 (salt stress) | Rice | Y08987 | CTGTCAC |
| Metabolism | | | |
| rubisco small | Maize | U09743 | CTGTCAC |
| rubisco small | *C. reinhardtii* | X04472 | CTGTCAC |
| Starch branching enzyme | Maize | AF072724 | CTGTCAC |
| ADP-glucose pyrophosphorylase | Barley | AJ239130 | CTGTCAC |
| ADP-glucose pyrophosphorylase | Potato | X96771 | CTGTCAC (2x) |
| Nitrate transporter | Barley | AF189727 | CTGTCAC |
| Sulphate transporter | Barley | AF075270 | CTGTCAC |
| chlorophyll a/b-binding protein | Wheat | X05823 | CTGTCAC |
| Others | | | |
| CDPK | Rice | Y13658 | TTGTCTC |
| | | | CTGTCAC |
| LAP (flower sp.) | Tomato | Y08305 | CTGTCAC |
| MADS box protein | Rice | AF204063 | CTGTCAC |
| GEG (fruit sp.) | *Gerbera hybrida* | AJ006273 | CTGTCAC |

TABLE 6

Proteins identified by two hybrid screening

| Nucleotide BLAST[a] | C.C.[b] | Protein BLAST[a] | C.C.[b] | Interaction Strength |
|---|---|---|---|---|
| Pti4 mRNA, tomato | 3.00E-93 | Pti4, tomato | 5.00E-26 | Strong |
| Pti4 mRNA, tomato | 0 | Pti4, tomato | 4.00E-39 | Strong |
| Pti4 mRNA, tomato | 1.00E-101 | Pti4, tomato | 6.00E-25 | Strong |
| cp29A mRNA, tobacco | 9.00E-72 | cp29 A, tobacco | 1.00E-33 | Medium |
| cp33 mRNA, tobacco | 5.00E-67 | cp33, tobacco | 2E-28 | Strong |
| B2 mRNA, carrot | 3.00E-13 | B2, carrot | 4.00E-09 | Medium |
| B2 mRNA, carrot | 2.00E-46 | B2, carrot | 1.00E-57 | Strong |
| B2 mRNA, carrot | 5.00E-37 | B2, carrot | 3.00E-28 | Strong |
| B2 mRNA, carrot | 1.00E-25 | B2, carrot | 9.00E-31 | Medium |
| B2 mRNA, carrot | 2.00E-37 | B2, carrot | 4.00E-29 | Medium |
| B2 mRNA, carrot | 2.00E-15 | B2, carrot | 8.00E-17 | Strong |
| B2 mRNA, carrot | 7.00E-49 | B2, carrot | 7.00E-52 | Medium |
| B2 mRNA, carrot | 4.00E-13 | B2, carrot | 3.00E-10 | Medium |
| B2 mRNA, carrot | 9.00E-11 | B2, carrot | 2.00E-06 | Strong |
| B2 mRNA, carrot | 1.00E-16 | B2, carrot | 2.00E-11 | Medium |
| None | — | B2-like | 0.44 | Weak |
| None | — | B2-like | 3.00E-09 | Weak |
| None | — | B2-like | 2.00E-28 | Weak |
| None | — | B2-like | 4.00E-25 | Medium |
| None | — | B2-like | 2.00E-15 | Weak |
| None | — | B2-like | 2.00E-05 | Medium |
| DB10 mRNA, tobacco | 2.00E-14 | RNA helicase, tobacco | 1.00E-04 | Strong |
| DB10 mRNA, tobacco | 0.73 | None | | Strong |
| DB10 mRNA, tobacco | 0 | RNA helicase, tobacco | 2.00E-90 | Strong |
| RZ-1 mRNA, tobacco | 1.00E-12 | RZ-1 RNA binding protein, tobacco | 0.075 | Strong |

[a]Results using the BLASTN ™ program for nucleotide BLAST ™ and BlastX ™ for protein BLAST ™ on the non redundant (nr) GenBank ™ database.
[b]C.C: Certainty Coefficient shows the probability that this particular sequence is chosen randomly.
[c]The strength of the interaction was qualitatively evaluated by coloration on X-gal containing media.

d) References

Arnon D. I. (1949). Plant Physiol 24:1–15.
Ausubel F. M. et al. (2001). Current Protocols in Molecular Biology. New York, Wiley.
Barnes, W. M. (1990). Proc. Natl. Acad. Sci. USA 87: 9183–9187.
Blumwald E. et al. (1998). Trends Plant Sci. 3: 342–346.
Brisson N. et al. (1989). Plant Cell 1: 559–566.
Burd C. G., Dreyfuss G. (1994). Science 265: 615–621.
Chen H. et al. (1998). J. Biol. Chem. 273: 31352–31357.
Dahlin C., Cline K. (1991). Plant Cell 3:1131–1140.
Després C., et al. (1995) Plant Cell 7: 589–598.
Desveaux D., et al. (2000) Plant Cell 12: 1477–1490.
Didier D. K., Klee H. J. (1992). Plant Mol. Biol. 18:977–979.
Dixon R. A., et al. (1994). 32: 479–501.
Gegenheimer P. (1990). Methods Enzymol. 182: 174–193.
Gross P., ap Rees, T. (1986). Planta 167:140–145.
Grosset J., et al. (1990). Plant Physiol. 92: 520–527.
Harlow, E., Lane, D. (1988). Antibodies: a laboratory manual. Cold Spring Harbor, N.Y., Cold Spring Harbor Laboratory Press.
Hirose, T., Sugiura, M. (2001). EMBO J. 20: 1144–1152.
Hucklesby D. P., et al. (1972). Planta 104: 220–233.
Israel, D. I. (1993). Nucl. Ac. Res. 21: 2627–2631.
Itadani, H., et al., (1994). Plant Mol. Biol. 24: 249–252.
Jouanneau, J.-P., et al. (1991). Plant Physiol. 96: 459–466.
Kamada, S. and Miwa, T. (1992). Gene 119: 229–236.
Laemmli, U. K. (1970) Nature 227: 680–685.
Lau, P. P., et al. (1997). J. Biol. Chem. 272: 1452–1455.
Lau, J. S., et al. (2000). J. Cell. Biochem. 79: 395–406.
Magnien, E., et al. (1980). Plant Sci. Letters 19: 231–241.
Matton, D. P., Brisson, N. (1989). Mol. Plant-Microbe Interact. 2: 325–331.
Matton, D. P., et al. (1993). Plant Mol. Biol. 22: 279–291.
Maxson, J. M., Woodson, W. R. (1996). Plant Mol. Biol. 31: 751–759.
Mayda, E., et a. (2000). Plant Cell 12: 2119–2128.
Michelotti, G. A. et al. (1996). Mol. Cell. Biol. 16: 2656–2669.
Mieszczak, M., et al. (1992). Mol. Gen. Genet. 234: 390–400.
Miflin, B. J. (1974). Plant Physiol. 54: 550–555.
Moiseyev, G. P., et al. (1994). Planta 193: 470–472.
Nakamura, T. et al. (1999). FEBS lett. 460: 437–441.
Nakamura, T., et al. (2001). J. Biol. Chem. 276: 147–152.
Ohta, M., et al. (1995). Plant. Mol. Bio. 27: 529–539.
Osmark, P., et al. (1998). Plant Mol. Biol. 38: 1243–1246.
Pelletier, J. N. et al. (1998). Proc. Natl. Acad. Sci. USA 95: 12141–12146.
Rothman-Denes, L. B., et al. (1998). Cold Spring Harbor Symposia on Quantitative Biology LXIII: 63–73.
Sambrook, J., Fritsch, E. F., Maniatis, T. (1989). Molecular cloning: a laboratory manual, $2^{nd}$ edition. Cold Spring Harbor, N.Y. Cold Spring Harbor Laboratory Press.
Séguin, A., et al. (1997). Plant Mol. Biol. 35: 281–291.
Smidt, M. P., et al. (1995). Nucl. Acids Res. 23: 2389–2395.
Smith, A. M., ap Rees T. (1979). Planta 146: 327–334.
Smith, D. B., Johnson, K. S. (1988). Gene 67: 31–40.
Somssich, I. E., Hahlbrock, K. (1998). Trends Plant Sci. 3: 86–90.
Swoboda, I., et al. (1996). Physiol. Plant. 96: 433–438.
Tang, X., Rolfe, S. A., Scholes, S. D. (1996). Plant Cell Env. 19: 967–975.

Tay, N., et al. (1992). J. Virol. 66: 6841–6848.

Tolnay, M., et al. (2000). Biochem. J. 348:151–158.

Ulmasov, T., et al. (1995). Plant Cell 7: 1611–1623.

Ulmasov, T., et al. (1999). Proc. Natl. Acad. Sci. USA 96: 5844–5849.

Van Loon, L. C., et al. (1994). Plant Mol. Bio. Rep. 12: 245–264.

Vinson, C. R., et al. (1988). Genes Dev. 2: 801–806.

Waegemann, K., Soil, J. (1996). J. Biol. Chem. 271: 6545–6554.

Ye L., et al. (1991). Nucl Acids Res. 19: 6485–6490.

Zhang, Y., et a. (1999) Proc. Natl. Acad. Sci. USA 96: 6523–6528

Zhou, J., et al. (1997). EMBO J. 16: 3207–3218.

While several embodiments of the invention have been described, it will be understood that the present invention is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

The invention claimed is:

1. A transformed or transfected cell comprising an isolated nucleic acid sequence encoding a protein having a SEBF (silencing element binding factor) function, wherein the nucleic acid sequence is selected from the group consisting of a nucleic acid sequence having SEQ ID NO: 21; and a nucleic acid sequence encoding the amino acid sequence of SEQ ID NO: 22.

2. A transformed or transfected cell comprising an isolated or purified protein having a SEBF function, said protein comprising an amino acid sequence selected from the group consisting of the amino acid sequence encoded by nucleotides 68 to 937 of SEQ ID NO: 21 and the amino acid sequence having SEQ ID NO: 22.

3. A cloning or expression vector, each comprising a nucleic acid sequence encoding a protein having a SEBF function, said nucleic acid sequence is selected from the group consisting of a nucleic acid sequence having SEQ ID NO: 21; and a nucleic acid sequence encoding the amino acid sequence of SEQ ID NO: 22.

4. The cloning or expression vector of claim 3, wherein it further comprises an inducible or constitutive promoter.

5. A transformed plant exhibiting an altered expression level or biological activity of a proteinic nuclear factor having a specific binding activity to BTGTCNC (SEQ ID NO: 23), wherein said transformed plant exhibits a modified resistance or tolerance to a pathogen when compared to a corresponding untransformed plant, and said proteinic nuclear factor is a polypeptide encoded by a nucleic acid sequence selected from the group consisting of a nucleic acid sequence having SEQ ID NO: 21; and a nucleic acid sequence encoding the amino acid sequence of SEQ ID NO: 22.

6. A transformed plant exhibiting an altered expression level or biological activity of a proteinic nuclear factor having a specific binding activity to BTGTCNC (SEQ ID NO: 23), wherein
    said transformed plant exhibits a modified resistance or tolerance to a pathogen when compared to a corresponding untransformed plant, and wherein
said proteinic nuclear factor is a SEBF protein comprising the amino acid sequence encoded by nucleotides 68 to 937 of SEQ ID NO: 21 and the amino acid sequence having SEQ ID NO: 22.

\* \* \* \* \*

```
                       SEQUENCE LISTING

<160> NUMBER OF SEQ ID NOS: 55

<210> SEQ ID NO 1
<211> LENGTH: 25
<212> TYPE: DNA
<213> ORGANISM: artificial sequence
<220> FEATURE:
<223> OTHER INFORMATION: Sequence is completely synthesized

<400> SEQUENCE: 1
tctagatcga attccgctcg accgg                                         25

<210> SEQ ID NO 2
<211> LENGTH: 25
<212> TYPE: DNA
<213> ORGANISM: artificial sequence
<220> FEATURE:
<223> OTHER INFORMATION: Sequence is completely synthesized

<400> SEQUENCE: 2
catggactgt cacttgtttt tttta                                         25

<210> SEQ ID NO 3
<211> LENGTH: 25
<212> TYPE: DNA
<213> ORGANISM: artificial sequence
<220> FEATURE:
<223> OTHER INFORMATION: Sequence is completely synthesized

<400> SEQUENCE: 3
tctagaagat cacttgtttt tttta                                         25

<210> SEQ ID NO 4
<211> LENGTH: 25
<212> TYPE: DNA
<213> ORGANISM: artificial sequence
<220> FEATURE:
<223> OTHER INFORMATION: Sequence is completely synthesized

<400> SEQUENCE: 4
tctagactgt cgagtgtttt tttta                                         25

<210> SEQ ID NO 5
<211> LENGTH: 25
<212> TYPE: DNA
<213> ORGANISM: artificial sequence
<220> FEATURE:
<223> OTHER INFORMATION: Sequence is completely synthesized
```

```
<400> SEQUENCE: 5
tctagactgt cacaactttt tttta                                          25

<210> SEQ ID NO 6
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 6
tcgcgactgt cacttgtttt tttt                                           24

<210> SEQ ID NO 7
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 7
tctatcctgt cacttgtttt tttt                                           24

<210> SEQ ID NO 8
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 8
tctagaaggt cacttgtttt tttt                                           24

<210> SEQ ID NO 9
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 9
tctagactac cacttgtttt tttt                                           24

<210> SEQ ID NO 10
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 10
tctagactgt cttttgtttt tttt                                           24

<210> SEQ ID NO 11
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 11
tctagactgt caagtgtttt tttt                                           24

<210> SEQ ID NO 12
<211> LENGTH: 24
```

```
<212> TYPE: DNA
<213> ORGANISM: artificial sequence
<220> FEATURE:
<223> OTHER INFORMATION: Sequence is completely synthesized

<400> SEQUENCE: 12
tctagactgt cactgttttt tttt                                              24

<210> SEQ ID NO 13
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 13
tctagaatgt cacttgtttt tttt                                              24

<210> SEQ ID NO 14
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 14
tctagacggt cacttgtttt tttt                                              24

<210> SEQ ID NO 15
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 15
tctagactat cacttgtttt tttt                                              24

<210> SEQ ID NO 16
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 16
tctagactga cacttgtttt tttt                                              24

<210> SEQ ID NO 17
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 17
tctagactgt gacttgtttt tttt                                              24

<210> SEQ ID NO 18
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 18
```

-continued tctagactgt cgcttgtttt tttt                                             24

<210> SEQ ID NO 19
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 19
tctagactgt caattgtttt tttt                                             24

<210> SEQ ID NO 20
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 20
tctagactgt cacgtgtttt tttt                                             24

<210> SEQ ID NO 21
<211> LENGTH: 1219
<212> TYPE: DNA
<213> ORGANISM: Solanum tuberosum
<220> FEATURE:
<221> NAME/KEY: CDS
<222> LOCATION: (68)..(937)
<223> OTHER INFORMATION:

<400> SEQUENCE: 21
gtttttcttt ttctgtcttc acaattcttt tgcttcaata aaaaccttat cttcaacccc      60 ttctcca atg gct tct tct tct tct tcc ctc cat ttc ctt tca ctt aca      109
        Met Ala Ser Ser Ser Ser Ser Leu His Phe Leu Ser Leu Thr
          1               5                  10 cca caa aca ctc cca aaa ccc act tcc caa aca act tca att tcc ttc      157
Pro Gln Thr Leu Pro Lys Pro Thr Ser Gln Thr Thr Ser Ile Ser Phe
 15                  20                  25                  30 ttt tca ctt cct cct tcc tct tta aac ctt tct tta tca tct tct tca      205
Phe Ser Leu Pro Pro Ser Ser Leu Asn Leu Ser Leu Ser Ser Ser Ser
                 35                  40                  45 acc cca aga aac ttc gaa tct tct cgt ttt gtt cgt aaa gta acc ctt      253
Thr Pro Arg Asn Phe Glu Ser Ser Arg Phe Val Arg Lys Val Thr Leu
             50                  55                  60 tct gat ttt gac caa att gag gaa gtt gag gct ggt gat gat gat gag      301
Ser Asp Phe Asp Gln Ile Glu Glu Val Glu Ala Gly Asp Asp Asp Glu
 65                  70                  75 gag gag ggg ggt ttg agt gat gaa ggt gct tca tat gaa gaa cgt aat      349
Glu Glu Gly Gly Leu Ser Asp Glu Gly Ala Ser Tyr Glu Glu Arg Asn
         80                  85                  90 gcc aat cct gac ctt aaa atc ttt gtt ggt aat ttg cct ttc agt gtt      397
Ala Asn Pro Asp Leu Lys Ile Phe Val Gly Asn Leu Pro Phe Ser Val
 95                 100                 105                 110 gac agt gcg gct ctt gct gag ctt ttt gag cgt gct gga gat gtt gaa      445
Asp Ser Ala Ala Leu Ala Glu Leu Phe Glu Arg Ala Gly Asp Val Glu
                115                 120                 125 atg gtt gag gtt atc tat gac aag ctt aca gga aga agc aga ggt ttt      493
Met Val Glu Val Ile Tyr Asp Lys Leu Thr Gly Arg Ser Arg Gly Phe
            130                 135                 140 ggc ttt gtg aca atg tcc tcc aaa gag gca gtt gaa gcc gcc tgt caa      541
Gly Phe Val Thr Met Ser Ser Lys Glu Ala Val Glu Ala Ala Cys Gln
        145                 150                 155

```
caa ttt aat ggc tat gaa att gac ggg agg gca ctg agg gtg aat tct    589
Gln Phe Asn Gly Tyr Glu Ile Asp Gly Arg Ala Leu Arg Val Asn Ser
        160                 165                 170 ggg cca gca cca ccc aaa agg gag aat tct ttc ggg gac aat tct tct    637
Gly Pro Ala Pro Pro Lys Arg Glu Asn Ser Phe Gly Asp Asn Ser Ser
175                 180                 185                 190 tac cag gga ggt agg ggt gga ggg agt atg gac agt tcc aac aga gtc    685
Tyr Gln Gly Gly Arg Gly Gly Gly Ser Met Asp Ser Ser Asn Arg Val
                195                 200                 205 tac gta gga aac ctt gca tgg agt gtt gac caa cag caa ctt gag acc    733
Tyr Val Gly Asn Leu Ala Trp Ser Val Asp Gln Gln Gln Leu Glu Thr
            210                 215                 220 ttg ttc agt gag caa gga aag gtc gtg gat gcc aaa gta gtc tat gat    781
Leu Phe Ser Glu Gln Gly Lys Val Val Asp Ala Lys Val Val Tyr Asp
        225                 230                 235 aga gat agc ggt aga tca agg ggc ttt gga ttt gta aca tac agt tcc    829
Arg Asp Ser Gly Arg Ser Arg Gly Phe Gly Phe Val Thr Tyr Ser Ser
    240                 245                 250 gct aag gag gtc aac gat gca att gaa agc ttg gat ggt gtt gac cta    877
Ala Lys Glu Val Asn Asp Ala Ile Glu Ser Leu Asp Gly Val Asp Leu
255                 260                 265                 270 ggt ggc agg gcc atc cgt gta agt cct gct gaa gct cgt cca ccc aga    925
Gly Gly Arg Ala Ile Arg Val Ser Pro Ala Glu Ala Arg Pro Pro Arg
                275                 280                 285 cgt caa ttc tga agattgtagc caacatcttt ttgaccgaga aaaggcttga        977
Arg Gln Phe gggtccagga ggtgacgata gttgcagaaa tgaatgagtt atgaactttg caacagctat  1037
cttaaacttg cgcggacaaa ctactctcta cttctggact aactagagct ctcaagtaaa  1097
ttagttttcg taatgtatgt tctgaaattg cctcaggaag aaattctgat cttgtaatat  1157
gattctatcc atcacttgtt gacagacaag acaatgaaaa agtttgatac tcttcgaaaa  1217
ag                                                                 1219

<210> SEQ ID NO 22
<211> LENGTH: 289
<212> TYPE: PRT
<213> ORGANISM: Solanum tuberosum

<400> SEQUENCE: 22

Met Ala Ser Ser Ser Ser Leu His Phe Leu Ser Leu Thr Pro Gln
1               5                   10                  15

Thr Leu Pro Lys Pro Thr Ser Gln Thr Thr Ser Ile Ser Phe Phe Ser
                20                  25                  30

Leu Pro Pro Ser Ser Leu Asn Leu Ser Leu Ser Ser Ser Thr Pro
            35                  40                  45

Arg Asn Phe Glu Ser Ser Arg Phe Val Arg Lys Val Thr Leu Ser Asp
    50                  55                  60

Phe Asp Gln Ile Glu Glu Val Glu Ala Gly Asp Asp Glu Glu Glu
65                  70                  75                  80

Gly Gly Leu Ser Asp Glu Gly Ala Ser Tyr Glu Glu Arg Asn Ala Asn
                85                  90                  95

Pro Asp Leu Lys Ile Phe Val Gly Asn Leu Pro Phe Ser Val Asp Ser
            100                 105                 110

Ala Ala Leu Ala Glu Leu Phe Glu Arg Ala Gly Asp Val Glu Met Val
        115                 120                 125

Glu Val Ile Tyr Asp Lys Leu Thr Gly Arg Ser Arg Gly Phe Gly Phe
```

```
            130                 135                 140
Val Thr Met Ser Ser Lys Glu Ala Val Glu Ala Ala Cys Gln Gln Phe
145                 150                 155                 160

Asn Gly Tyr Glu Ile Asp Gly Arg Ala Leu Arg Val Asn Ser Gly Pro
            165                 170                 175

Ala Pro Pro Lys Arg Glu Asn Ser Phe Gly Asp Asn Ser Ser Tyr Gln
            180                 185                 190

Gly Gly Arg Gly Gly Gly Ser Met Asp Ser Ser Asn Arg Val Tyr Val
            195                 200                 205

Gly Asn Leu Ala Trp Ser Val Asp Gln Gln Gln Leu Glu Thr Leu Phe
            210                 215                 220

Ser Glu Gln Gly Lys Val Val Asp Ala Lys Val Val Tyr Asp Arg Asp
225                 230                 235                 240

Ser Gly Arg Ser Arg Gly Phe Gly Phe Val Thr Tyr Ser Ser Ala Lys
            245                 250                 255

Glu Val Asn Asp Ala Ile Glu Ser Leu Asp Gly Val Asp Leu Gly Gly
            260                 265                 270

Arg Ala Ile Arg Val Ser Pro Ala Glu Ala Arg Pro Pro Arg Arg Gln
            275                 280                 285

Phe

<210> SEQ ID NO 23
<211> LENGTH: 7
<212> TYPE: DNA
<213> ORGANISM: artificial sequence
<220> FEATURE:
<223> OTHER INFORMATION: Sequence is completely synthesized
<220> FEATURE:
<221> NAME/KEY: misc_feature
<222> LOCATION: (1)..(1)
<223> OTHER INFORMATION: "B" represents a "T", a "C" or a "G"
<220> FEATURE:
<221> NAME/KEY: misc_feature
<222> LOCATION: (6)..(6)
<223> OTHER INFORMATION: "N" represents a "A", a "T", a "C" or a "G"

<400> SEQUENCE: 23 btgtcnc                                                                7

<210> SEQ ID NO 24
<211> LENGTH: 7
<212> TYPE: DNA
<213> ORGANISM: artificial sequence
<220> FEATURE:
<223> OTHER INFORMATION: Sequence is completely synthesized
<220> FEATURE:
<221> NAME/KEY: misc_feature
<222> LOCATION: (1)..(1)
<223> OTHER INFORMATION: "Y" represents a "T" or a "C"
<220> FEATURE:
<221> NAME/KEY: misc_feature
<222> LOCATION: (6)..(6)
<223> OTHER INFORMATION: "N" represents a "A", a "G", a "T" or a "C"

<400> SEQUENCE: 24 ytgtcnc                                                                7

<210> SEQ ID NO 25
<211> LENGTH: 7
<212> TYPE: DNA
<213> ORGANISM: Solanum tuberosum

<400> SEQUENCE: 25
```

```
ctgtcac                                                              7
```

<210> SEQ ID NO 26
<211> LENGTH: 9
<212> TYPE: DNA
<213> ORGANISM: Solanum tuberosum

<400> SEQUENCE: 26

```
gactgtcac                                                            9
```

<210> SEQ ID NO 27
<211> LENGTH: 39
<212> TYPE: DNA
<213> ORGANISM: artificial sequence
<220> FEATURE:
<223> OTHER INFORMATION: Sequence is completely synthesized

<400> SEQUENCE: 27

```
gccaagcttt agataaaatg acacaaatgt caaaaatgg                           39
```

<210> SEQ ID NO 28
<211> LENGTH: 24
<212> TYPE: DNA
<213> ORGANISM: artificial sequence
<220> FEATURE:
<223> OTHER INFORMATION: Sequence is completely synthesized

<400> SEQUENCE: 28

```
ccacccgggg atccagcttt gaac                                           24
```

<210> SEQ ID NO 29
<211> LENGTH: 20
<212> TYPE: DNA
<213> ORGANISM: artificial sequence
<220> FEATURE:
<223> OTHER INFORMATION: Sequence is completely synthesized

<400> SEQUENCE: 29

```
cagtccatgg ttaaatcaac                                                20
```

<210> SEQ ID NO 30
<211> LENGTH: 20
<212> TYPE: DNA
<213> ORGANISM: artificial sequence
<220> FEATURE:
<223> OTHER INFORMATION: Sequence is completely synthesized

<400> SEQUENCE: 30

```
taaccatgga ctgtcacttg                                                20
```

<210> SEQ ID NO 31
<211> LENGTH: 29
<212> TYPE: DNA
<213> ORGANISM: artificial sequence
<220> FEATURE:
<223> OTHER INFORMATION: Sequence is completely synthesized

<400> SEQUENCE: 31

```
gccgcaagtt ttctgcagtg tttttgctc                                      29
```

<210> SEQ ID NO 32
<211> LENGTH: 27
<212> TYPE: DNA
<213> ORGANISM: artificial sequence
<220> FEATURE:
<223> OTHER INFORMATION: Sequence is completely synthesized

```
<400> SEQUENCE: 32
ggtttggatc cagtagtaaa gtggcga                                          27

<210> SEQ ID NO 33
<211> LENGTH: 21
<212> TYPE: DNA
<213> ORGANISM: artificial sequence
<220> FEATURE:
<223> OTHER INFORMATION: Sequence is completely synthesized

<400> SEQUENCE: 33
atgtctactc ctgcgctcat t                                                21

<210> SEQ ID NO 34
<211> LENGTH: 41
<212> TYPE: PRT
<213> ORGANISM: Solanum tuberosum
<220> FEATURE:
<221> NAME/KEY: MISC_FEATURE
<222> LOCATION: (37)..(37)
<223> OTHER INFORMATION: "Xaa" is unknown

<400> SEQUENCE: 34

Val Thr Leu Ser Asp Phe Asp Gln Ile Glu Glu Val Glu Ala Gly Asp
1               5                  10                  15

Asp Asp Glu Glu Glu Gly Gly Leu Ser Asp Glu Ala Gly Ala Ser Tyr
            20                  25                  30

Glu Glu Arg Asn Xaa Asn Pro Asp Leu
        35                  40

<210> SEQ ID NO 35
<211> LENGTH: 23
<212> TYPE: DNA
<213> ORGANISM: artificial sequence
<220> FEATURE:
<223> OTHER INFORMATION: Sequence is completely synthesized
<220> FEATURE:
<221> NAME/KEY: misc_feature
<222> LOCATION: (9)..(9)
<223> OTHER INFORMATION: "n" corresponds to a modified base: Inosine
<220> FEATURE:
<221> NAME/KEY: misc_feature
<222> LOCATION: (12)..(12)
<223> OTHER INFORMATION: "n" corresponds to a modified base: Inosine

<400> SEQUENCE: 35
gtkacwytnt cngatttyga yca                                              23

<210> SEQ ID NO 36
<211> LENGTH: 20
<212> TYPE: DNA
<213> ORGANISM: artificial sequence
<220> FEATURE:
<223> OTHER INFORMATION: Sequence is completely synthesized
<220> FEATURE:
<221> NAME/KEY: misc_feature
<222> LOCATION: (9)..(9)
<223> OTHER INFORMATION: "n" corresponds to a modified base: Inosine

<400> SEQUENCE: 36
arrttwccna craaratytt                                                  20

<210> SEQ ID NO 37
<211> LENGTH: 19
<212> TYPE: DNA
<213> ORGANISM: artificial sequence
```

```
<220> FEATURE:
<223> OTHER INFORMATION: Sequence is completely synthesized

<400> SEQUENCE: 37
gtttgagtga tgaaggtgc                                                    19

<210> SEQ ID NO 38
<211> LENGTH: 30
<212> TYPE: DNA
<213> ORGANISM: artificial sequence
<220> FEATURE:
<223> OTHER INFORMATION: Sequence is completely synthesized

<400> SEQUENCE: 38
gccgttctgt cttcacaatt cttttgcttc                                        30

<210> SEQ ID NO 39
<211> LENGTH: 30
<212> TYPE: DNA
<213> ORGANISM: artificial sequence
<220> FEATURE:
<223> OTHER INFORMATION: Sequence is completely synthesized

<400> SEQUENCE: 39
caacatctcc agcacgctca aaaagctcag                                        30

<210> SEQ ID NO 40
<211> LENGTH: 30
<212> TYPE: DNA
<213> ORGANISM: artificial sequence
<220> FEATURE:
<223> OTHER INFORMATION: Sequence is completely synthesized

<400> SEQUENCE: 40
cctctgcttc ttcctgtaag cttgtcatag                                        30

<210> SEQ ID NO 41
<211> LENGTH: 30
<212> TYPE: DNA
<213> ORGANISM: artificial sequence
<220> FEATURE:
<223> OTHER INFORMATION: Sequence is completely synthesized

<400> SEQUENCE: 41
cagttgaagc cgcctgtcaa caatttaatg                                        30

<210> SEQ ID NO 42
<211> LENGTH: 30
<212> TYPE: DNA
<213> ORGANISM: artificial sequence
<220> FEATURE:
<223> OTHER INFORMATION: Sequence is completely synthesized

<400> SEQUENCE: 42
ttgacgggag ggcactgagg gtgaattctg                                        30

<210> SEQ ID NO 43
<211> LENGTH: 29
<212> TYPE: DNA
<213> ORGANISM: artificial sequence
<220> FEATURE:
<223> OTHER INFORMATION: Sequence is completely synthesized

<400> SEQUENCE: 43
gctttcaatt gcatcgttga cctccttag                                         29
```

<210> SEQ ID NO 44
<211> LENGTH: 30
<212> TYPE: DNA
<213> ORGANISM: artificial sequence
<220> FEATURE:
<223> OTHER INFORMATION: Sequence is completely synthesized

<400> SEQUENCE: 44
gcttcagcag gacttacacg gatggccctg                              30

<210> SEQ ID NO 45
<211> LENGTH: 25
<212> TYPE: DNA
<213> ORGANISM: Solanum tuberosum

<400> SEQUENCE: 45
tctagactgt cacttgtttt tttta                                   25

<210> SEQ ID NO 46
<211> LENGTH: 24
<212> TYPE: DNA
<213> ORGANISM: Solanum tuberosum

<400> SEQUENCE: 46
tctagactgt cacttgtttt tttt                                    24

<210> SEQ ID NO 47
<211> LENGTH: 25
<212> TYPE: DNA
<213> ORGANISM: Solanum tuberosum

<400> SEQUENCE: 47
tctagactgt cacttgtttt tttta                                   25

<210> SEQ ID NO 48
<211> LENGTH: 25
<212> TYPE: DNA
<213> ORGANISM: Solanum tuberosum

<400> SEQUENCE: 48
aacatctgct ttgtcaccct ccttg                                   25

<210> SEQ ID NO 49
<211> LENGTH: 25
<212> TYPE: DNA
<213> ORGANISM: Nicotiana tabacum

<400> SEQUENCE: 49
attaagccat gtctccatca tcttc                                   25

<210> SEQ ID NO 50
<211> LENGTH: 7
<212> TYPE: DNA
<213> ORGANISM: Solanum tuberosum

<400> SEQUENCE: 50 ctgtcac                                                        7

<210> SEQ ID NO 51
<211> LENGTH: 7
<212> TYPE: DNA
<213> ORGANISM: Glycine max

```
<400> SEQUENCE: 51 ttgtctc                                                                 7

<210> SEQ ID NO 52
<211> LENGTH: 21
<212> TYPE: DNA
<213> ORGANISM: Nicotiana tabacum

<400> SEQUENCE: 52
taagccatgt ctccatcatc t                                                21

<210> SEQ ID NO 53
<211> LENGTH: 21
<212> TYPE: DNA
<213> ORGANISM: artificial sequence
<220> FEATURE:
<223> OTHER INFORMATION: Sequence is completely synthesized

<400> SEQUENCE: 53
taagccctgt ctccatcatc t                                                21

<210> SEQ ID NO 54
<211> LENGTH: 21
<212> TYPE: DNA
<213> ORGANISM: artificial sequence
<220> FEATURE:
<223> OTHER INFORMATION: Sequence is completely synthesized

<400> SEQUENCE: 54
taagccatat ctccatcatc t                                                21

<210> SEQ ID NO 55
<211> LENGTH: 6
<212> TYPE: DNA
<213> ORGANISM: artificial sequence
<220> FEATURE:
<223> OTHER INFORMATION: Sequence is completely synthesized
<220> FEATURE:
<221> NAME/KEY: misc_feature
<222> LOCATION: (5)..(5)
<223> OTHER INFORMATION: n represents an "A", a "T", a "C" or a "G"

<400> SEQUENCE: 55 tgtcnc                                                                  6
```